United States Patent [19]
Neely et al.

[11] Patent Number: 5,697,379
[45] Date of Patent: Dec. 16, 1997

[54] METHOD AND APPARATUS FOR OBJECTIVE AND AUTOMATED ANALYSIS OF AUDITORY BRAINSTEM RESPONSE TO DETERMINE HEARING CAPACITY

[76] Inventors: Stephen T. Neely, 10619 N. 51st St., Omaha, Nebr. 68152; Margaret Sullivan Pepe, 5726 26th Ave. NE., Seattle, Wash. 98105

[21] Appl. No.: 493,326

[22] Filed: Jun. 21, 1995

[51] Int. Cl.$^6$ ............................................. A61B 5/04
[52] U.S. Cl. ............................. 128/731; 128/746
[58] Field of Search ........................ 128/731, 746; 73/585

[56] References Cited

U.S. PATENT DOCUMENTS 5,230,344 7/1993 Ozdamar et al. ............ 128/731
5,282,475 2/1994 Urbach.

OTHER PUBLICATIONS

M. Don, C. Elberling, and M. Waring; "Objective Detection of Averaged Auditory Brainstem Responses," *Scandinavian Audiology*, vol. 13, pp. 219–228, 1984.

"Estimation of Auditory Brainstem Response, ABR, by Means of Bayesian Inference," *Scandinavian Audiology*, vol. 14, pp. 89–96, 1985.

*Primary Examiner*—Vincent Millin
*Assistant Examiner*—Robert N. Wieland
*Attorney, Agent, or Firm*—John A. Beehner Law Office; John A. Beehner

[57] ABSTRACT

An improved method of gathering and analyzing auditory brainstem response (ABR) data to objectively determine the hearing capacity of an individual. The steps include generating and transmitting a plurality of hearing stimuli to the test individual and receiving the ABR signal data therefrom. The ABR signal data consists of a series of ABR waveforms, each of the waveforms being associated with a respective one of the stimuli. A concurrent replication of the ABR waveforms may be formed to indicate reliability of the data by maintaining two buffers, each of the buffers comprising ABR signal data from alternating ABR waveforms. The received ABR waveforms are analyzed to determine the hearing capacity of the individual. The analysis of the received ABR waveform may be accomplished using a computer routine incorporating new algorithms for the estimation of noise present in the ABR signal. The analysis may be further enhance by comparing the ABR signal estimate with a benchmark template formed from ABR data of good hearing subjects.

39 Claims, 20 Drawing Sheets

| | | |
|---|---|---|
| .4095988 STIM=0, TFSPLA 5.232983 | .6756765 STIM=0, TFMP 7.022305 | .6868796 STIM=0, TWTJFMP 8.42071 |
| .4095988 STIM=1, TFSPLA 5.232983 | .6756765 STIM=1, TFMP 7.022305 | .6868796 STIM=1, TWTJFMP 8.42071 |
| FSP | FMP | WTJFMP |
| .2826799 STIM=0, TCORRS 16.23159 | .3945366 STIM=0, TCWFMP 8.42071 | .0221076 STIM=0, TSCOR 6.22426 |
| .2826799 STIM=1, TCORRS 16.23159 | .3945366 STIM=1, TCWFMP 8.42071 | .0221076 STIM=1, TSCOR 6.22426 |
| CORRS | CWFMP | SCOR | weight=var(SP), 2-15ms window, truncated

Figure 8

FALSE POSITIVES

METHOD AND APPARATUS FOR OBJECTIVE AND AUTOMATED ANALYSIS OF AUDITORY BRAINSTEM RESPONSE TO DETERMINE HEARING CAPACITY

BACKGROUND OF THE INVENTION

1. Technical Field

The method and apparatus of the present invention relate generally to an apparatus and method to objectively determine the hearing capacity, especially of small infants. More specifically, it relates to an apparatus and method of utilizing the auditory brainstem response (ABR) to hearing stimuli in conjunction with a quantitative test criterion, to automate the hearing test procedure as much as possible. It also relates to a method and apparatus for conducting hearing testing which removes the subjectivity of the tester from the analysis process. It further relates to a method and apparatus which obviates the necessity for an expert observer to monitor and evaluate the test procedure and results and allows the test to be terminated upon achievement of the test criterion.

Currently, an expert must observe the ABR test procedure and evaluate the results after a rather lengthy test procedure. While several statistical tools have been developed in the past to in some way automate or assist this expert observer in his or her analysis of the results, the accuracy of these statistical aids has fallen short. In many cases, the prior art statistical methods can give results which are diametrically opposed to the actual hearing condition of the tested individual (i.e. false passes).

The auditory brainstem response (ABR) has been known for about 40 years and is widely used in the clinical evaluation of hearing. The simplest description of this technique is that an auditory stimulus such as a click or the like, is introduced into the patient's ear. Neural activity, in the form of a wave pattern, is then monitored. It was discovered that a certain neural waveform benchmark pattern occurs in normal hearing persons in response to such stimuli. Therefore, the tested individual's neural activity is checked for this pattern. If the tested person's neural waveform matches this benchmark pattern, it may be accurately concluded that this person enjoys normal hearing. Until the present invention, however, it has been left to a visual inspection of the patient's waveform to determine existence of a match. The method of the present invention allows this determination to be made quantitatively without the need for the subjective conclusion of an expert observer.

ABRs can provide information about the functional integrity of the auditory system and can be used to predict the pure tone audiogram. ABR measurements are especially useful for patients who are difficult to test by conventional behavioral audiometry, such as infants and developmentally delayed individuals, since they can not verbally relate that the sound was heard.

The ABR has been recommended by a National Institute of Health (NIH) consensus panel as a screening test for hearing loss in infants. Methods for the objective detection and analysis of the ABR are currently under investigation which will enhance its usefulness as a screening test. Additionally, the U.S. government is currently studying regulations which would require auditory testing of all infants. Such universal testing would not be economically feasible without greatly automating the analysis procedure and eliminating the need for experts to observe the tests and analyze the results. This needed automation is provided by the present invention.

Auditory evoked potentials (such as the ABR) can be recorded from surface electrodes on the scalp in response to auditory stimulation. As a practical matter, in addition to the ABR, the electrodes will also record unwanted potentials due to other ongoing neural activity, muscle activity, and nonphysiological, environmental sources. The primary technical problem in recording the ABR is to identify and minimize the influence of these unwanted potentials which are referred to collectively as background or residual noise.

Therefore, there are two components to ABR testing. First, is to examine the neural activity produced by the brainstem and monitored by the electrodes. Secondly, since this activity occurs in the presence of noise, both internal and environmental, this noise must be accounted for in order to arrive at an accurate representation of the actual brainstem signal.

One of the most common methods of analyzing signals occurring in noise is to construct a signal-to-noise variance ratio. Obviously one must arrive at an accurate estimation of the noise level in order to construct such a ratio. Clearly, the accuracy of the ratio and the validity of any conclusions drawn therefrom is greatly impacted by the accuracy of the noise estimate.

A major advance in the art presented by the present invention relates to an improved estimate of this residual noise, as well as an improved method of analyzing the ABR signal.

2. Description of the Prior Art

As mentioned above, the estimator used to estimate the noise component in the signal has a great impact on the accuracy and validity of the conclusions drawn therefrom. One of the most popular current noise estimators is the mean sum of squares (mss). Tests, described in detail below, have been run on this noise estimator in conjunction with known ABR samples.

These test results have important implications for objective detection of the ABR. The current mean sum of squares estimator of noise appears to be biased too large. This makes the signal-to-noise ratio biased too small, and hence the current detection method is less sensitive to the ABR signal than it ought to be. Since termination of the test is dependent on the signal detection method, increased test time is a consequence.

The analyses described below demonstrate that there is considerable dependence among data points obtained relatively close in time. Thus, the independence assumption upon which the usual residual noise estimate relies does not hold.

In the ABR test system, substantial autocorrelations among single point values were found which rendered invalid the prior art method (mss) of estimating residual noise. The exact sources of these autocorrelations is unknown but clearly any noise nonuniformly distributed in frequency and which lasts for several sweeps can induce such correlation.

Faster and more accurate detection, which is particularly important for large scale screening programs, is achieved by replacing the usual estimate of residual noise by the improved estimator of the present invention.

The improved ("SCOR") estimator of the present invention uses the signal estimator and noise estimator in conjunction with the cross-correlation between the observed data and a benchmark waveform template. The benchmark waveform template was prepared by averaging together ABR waveforms from a large number of normal hearing subjects. The template therefore provides a master against which future test data may be compared.

Thus, the improved signal detection method of the present invention incorporates not only a vastly improved estimator for the noise component of the detection method but also compares this improved signal-to-noise estimator with a master template in order to arrive at an algorithm statistic which provides the test taker with a definitive quantitative indication of the hearing capacity of the tested subject.

It has been determined from testing described below that a SCOR value greater than a certain threshold value is indicative of good hearing. Thus, the test may be conducted by monitoring this SCOR value and as soon as its value exceeds this threshold, the test may be terminated and the individual's hearing judged normal.

Therefore, it is a primary objective of the present invention to provide a more precise statistical estimate of the background residual noise present in an ABR test procedure.

A further objective of the present invention is to provide a method and apparatus for automating the conduct of a hearing test based upon the auditory brainstem response.

A further objective of the present invention is to provide a method and apparatus for objectively automating the gathering and analysis of data from a hearing test based on the auditory brainstem response to hearing stimuli.

Yet another objective is to provide a method and apparatus which is capable of acquiring and analyzing the data so as to provide a quantitative indication of hearing threshold detection thereby eliminating the need for an expert observer to oversee and analyze the test results.

SUMMARY OF THE INVENTION

The present invention is directed to an improved method of gathering and analyzing auditory brainstem response (ABR) data to objectively determine the hearing capacity of an individual. The steps include generating and transmitting a plurality of hearing stimuli to the test individual and receiving the ABR signal data therefrom. The ABR signal data consists of a series of ABR waveforms, each of the waveforms being associated with a respective one of the stimuli. A concurrent replication of the ABR waveforms may be formed to indicate reliability of the data and to facilitate statistical analysis, by maintaining two buffers, each of the buffers comprising ABR signal data from alternating ABR waveforms. The received ABR waveforms are analyzed to determine the hearing capacity of the individual.

The analysis of the received ABR waveform may be accomplished using a computer routine incorporating new algorithms for the estimation of noise present in the ABR signal. The analysis may be further enhanced by comparing the ABR signal estimate with a benchmark template formed from ABR data of good hearing subjects.

BRIEF DESCRIPTION OF THE DRAWINGS

FIG. 4 is a graph illustrating the oscillation between data points between sweeps on test baby number 4.

FIG. 5 is a scattergram illustrating the data shown in FIG. 4.

FIGS. 7–14 relate to test data taken in conjunction with development of the new invention method and its comparison to prior art methods.

FIG. 7 is a graph illustrating the 6 analysis statistics with the upper row corresponding to the "no-stim" data and the lower row corresponding to the "stim" data and using a 2–35 ms window and var(SP) weighing.

FIG. 8 is a graph illustrating the 6 analysis statistics with the upper row corresponding to the "no-stim" data and the lower row corresponding to the "stim" data and using a 2–15 ms window and var(SP) weighing.

FIG. 9 is a graph illustrating the 6 statistics with the upper row corresponding to the "no-stim" data and the lower row corresponding to the "stim" data and using a 2–15 ms window and sd(SP) weighing.

FIGS. 10a–d are graphs illustrating the average ABR waveform for four babies exhibiting a "false-pass" during the testing.

FIG. 11 is a graph showing the ABR waveform for baby 4 in the test group.

FIG. 13 is a graph illustrating the results of the test using the prior art FSP statistic.

FIG. 14 is a graph illustrating the results of the test using the improved SCOR detection statistic of the present invention.

DESCRIPTION OF THE PREFERRED EMBODIMENT

Figure 12A:
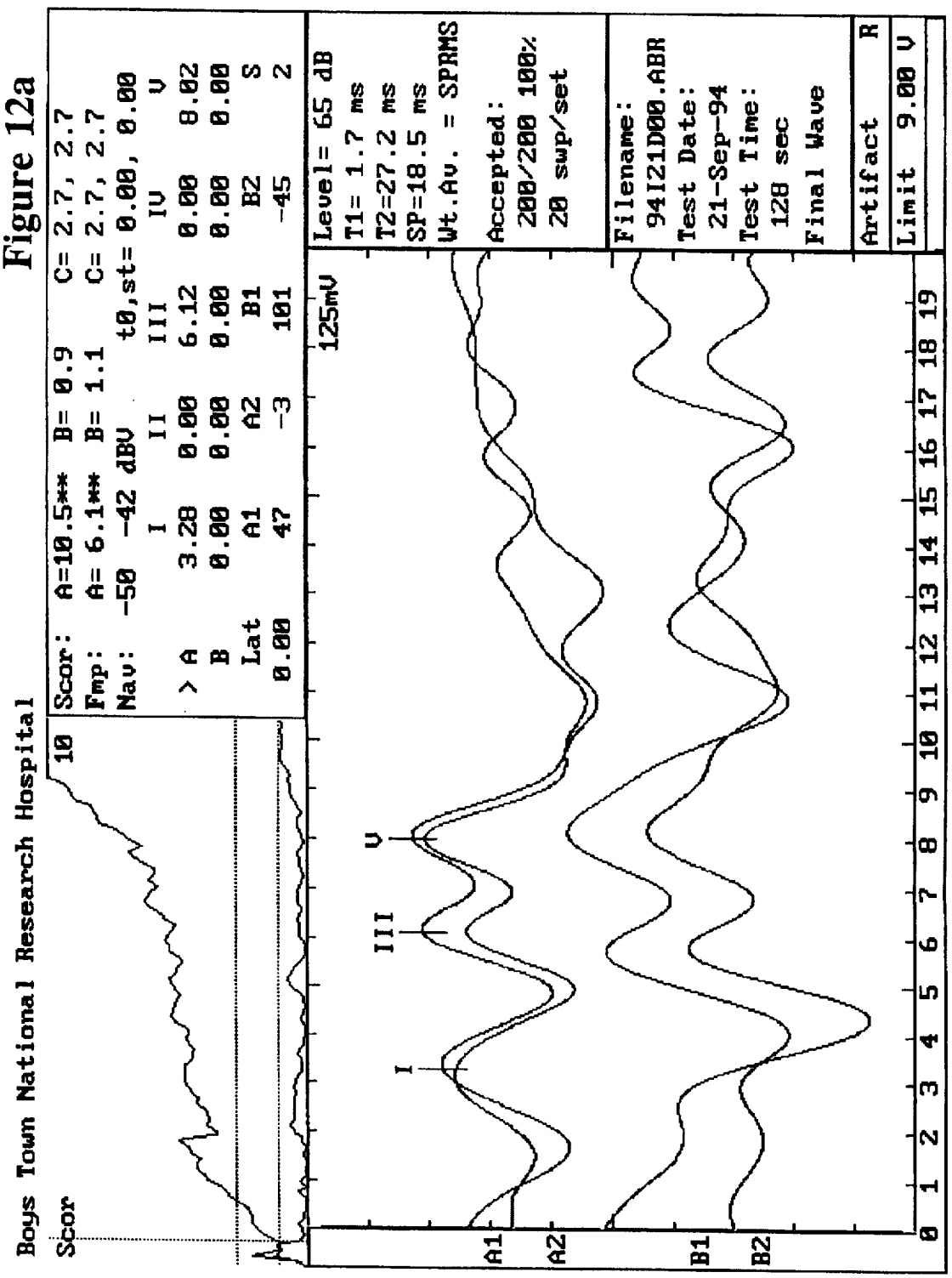
FIG. 12a illustrates the display output of the computer routine of the present invention in a (hearing) stimulus environment, including typical concurrently replicated ABR waveforms of a normal hearing subject from the mastoid/vertex and C7/vertex regions and a display of the SCOR statistic applied to the mastoid and C7 waveforms.
Figure 12B:
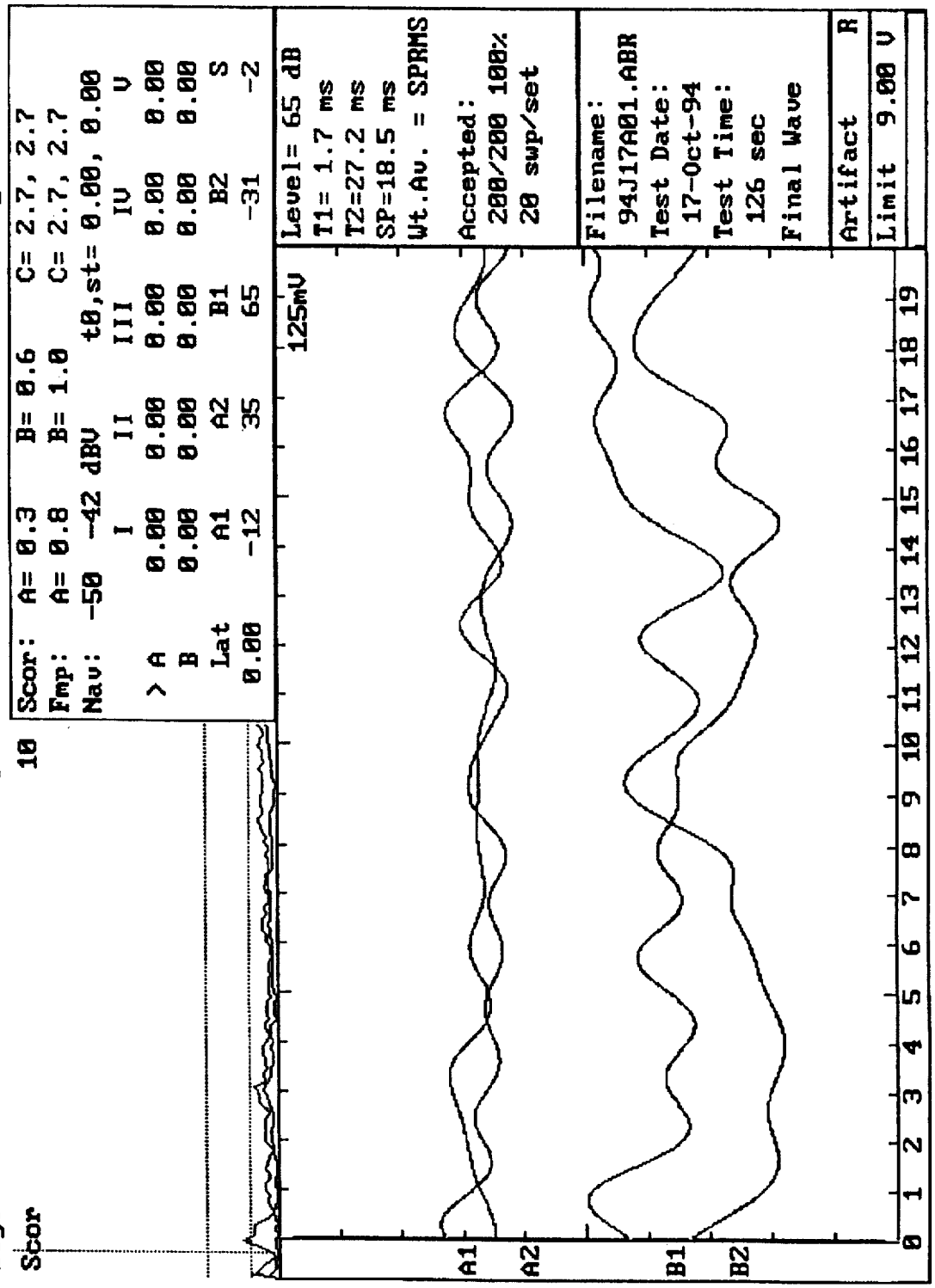
FIG. 12b is a display output of the same baby used in FIG. 12a but in the nonstimulus environment.

The principle objective in the present invention is to provide an apparatus and method capable of utilizing the auditory brainstem response in connection with hearing stimuli to provide a means of objectively determining the person's hearing capacity. Since the auditory brainstem response (ABR) is a predictable waveform pattern (36a and 36b, FIG. 12a) known to occur in normal hearing individuals, a method should be available to look for this predictable response and to provide an indication thereof. The identity of a normal hearing ABR waveform is indicated by the presence of the I, III and V peaks in the mastoid waveforms 36a and 36b. Such a method and apparatus able to detect this auditory brainstem response to hearing stimuli, would greatly automate, simplify, and expedite testing procedures for this targeted group. Note that while the method and apparatus of the present invention is capable of acquiring, analyzing and displaying data from other electrode positions such as C7 (37a and 37b FIG. 12a), we have found the mastoid/vertex data (36a and 36b) to be most useful in hearing testing. FIG. 12b illustrates the display associated with a non-stimulus (non-hearing) individual. A comparison between the waveform displayed in FIG. 12a and that of FIG. 12b, clearly illustrates the difference in appearance between the hearing (12a) and non-hearing (12b) waveforms.

As mentioned, the ABR response is a predictable looking waveform of neural activity which, in normal hearing individuals, occurs as a result of and in response to hearing stimuli. As also mentioned, this ABR signal occurs in the presence of continuous noise. Such noise occurs as the result of muscle activity and other physiological activity as well as nonphysiological, environmental sources such as 60 Hz line noise and the like. Therefore, in hearing impaired individuals the ABR signal will be absent but the noise will remain. Clearly, it is important to be able to accurately model this residual background noise so as to be able to ascertain whether the ABR signal is present.

One method of objectively and quantitatively determining the presence of the ABR signal is to form an estimate of the signal from the observed data, an estimate of the noise, and computing a signal-to-noise ratio (SNR) therefrom.

The present invention utilizes a unique and novel method of estimating the signal and noise, and computing a signal-to-noise ratio which is extremely accurate in objectively and quantitatively indicating pass/fail hearing capacity. The novel signal analysis method incorporates a threshold value, indicated as the horizontal line 40 in FIG. 12a, the exceeding of which by the SCOR statistic, see point 42 on line 38, is indicative of normal hearing capacity. Conversely, FIG. 12b illustrates the display associated with a non-hearing individual. As is seen clearly in the Figure, the shape of the waveforms 136a and 136b displayed in FIG. 12b is very different from 36a and 36b in FIG. 12a. Additionally, is seen that the value 138 of the SCOR statistic never crosses the threshold line 140 and whose final value 139 is less that this threshold value, indicating a lack of normal hearing.

The numerical value of the threshold is not necessarily a constant, unique number applicable to all situations. Rather it must take into account the signal processing performed on the data. For example, in one situation, a threshold value of 1.5 may signify normal hearing, whereas if additional digital filtering is performed, the threshold value may be chosen as 2.7. Details of this digital filtering are discussed below in connection with development of the SCOR analysis method. The precise value of the threshold is not as important as the fact that a value may be chosen, given the testing data manipulations, which indicates good hearing.

a. ABR Testing Apparatus and Procedure

As referenced above in connection with the prior art, signal and noise estimates have previously been developed for the analysis of the ABR. In conjunction with the development of the test and analysis method and apparatus of the present invention, these prior art methods, as well as the present invention, were analyzed for accuracy in results on a known sample of individuals. These test procedures and results will now be discussed in detail.

Figure 1:
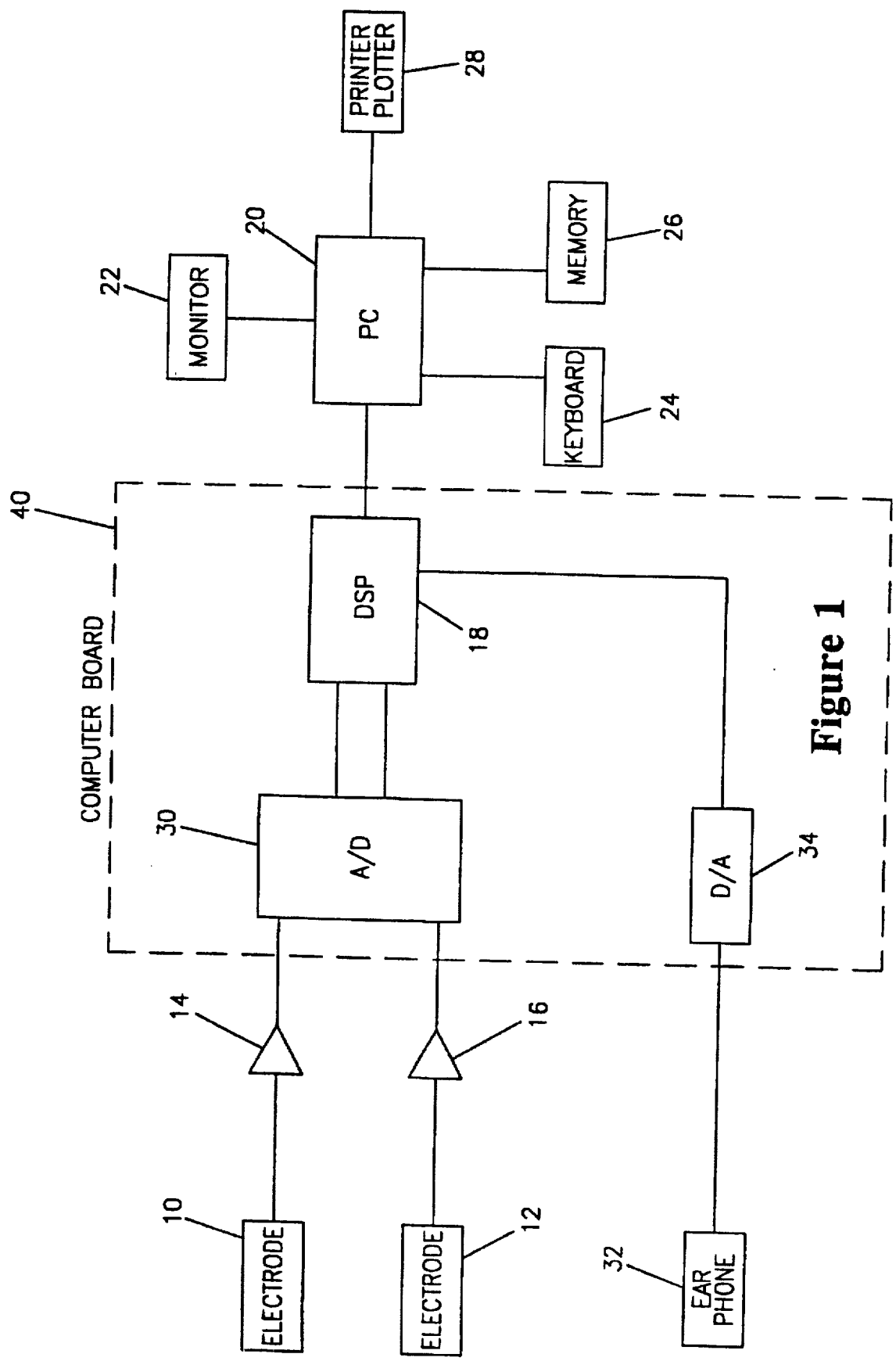
FIG. 1 is a block diagram of the components of the ABR test apparatus of the present invention.
Figure 15:
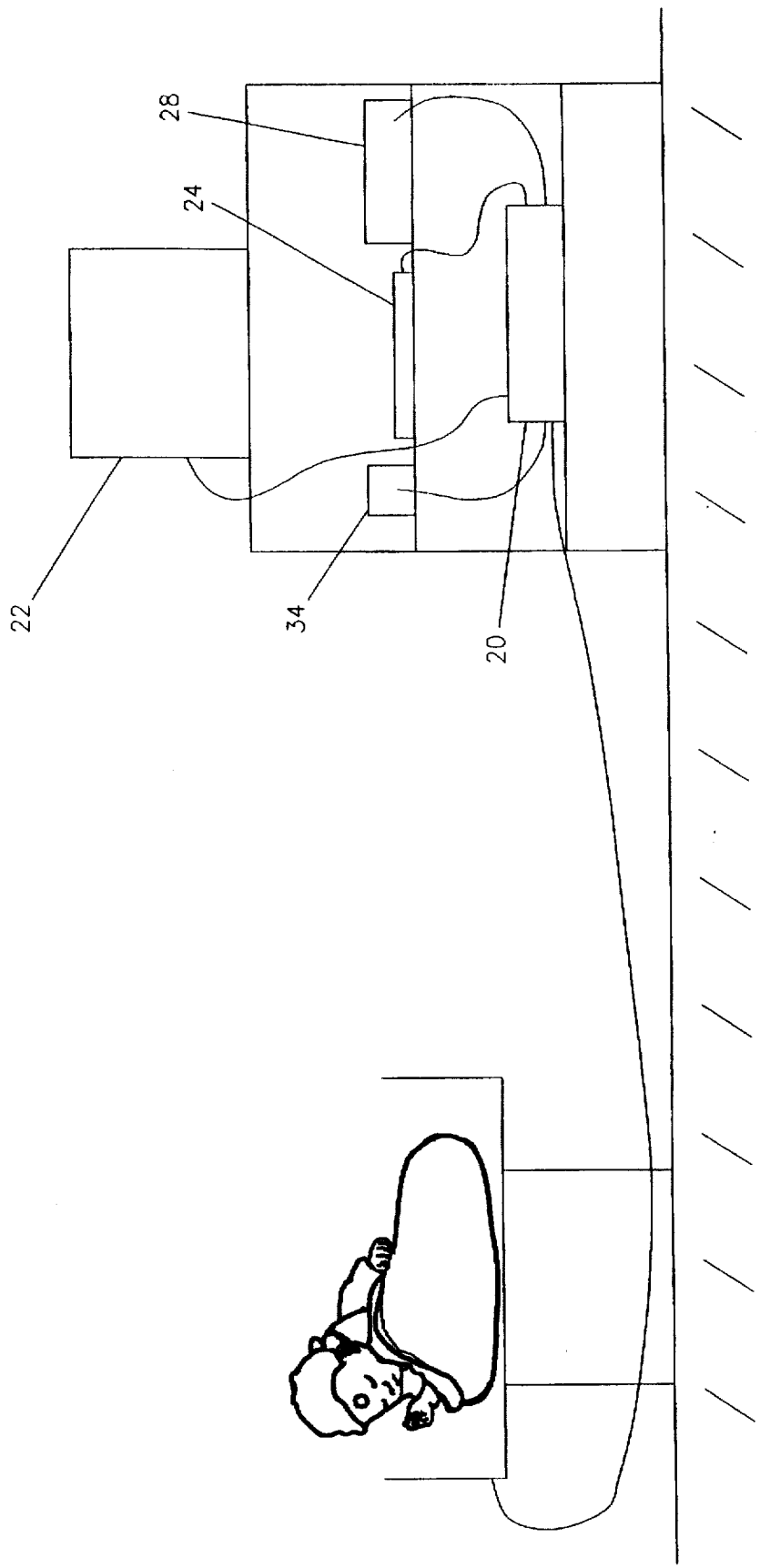
FIG. 15 is an illustration of the test apparatus and environment in which the hearing tests are conducted according to the present invention.
Figure 16:
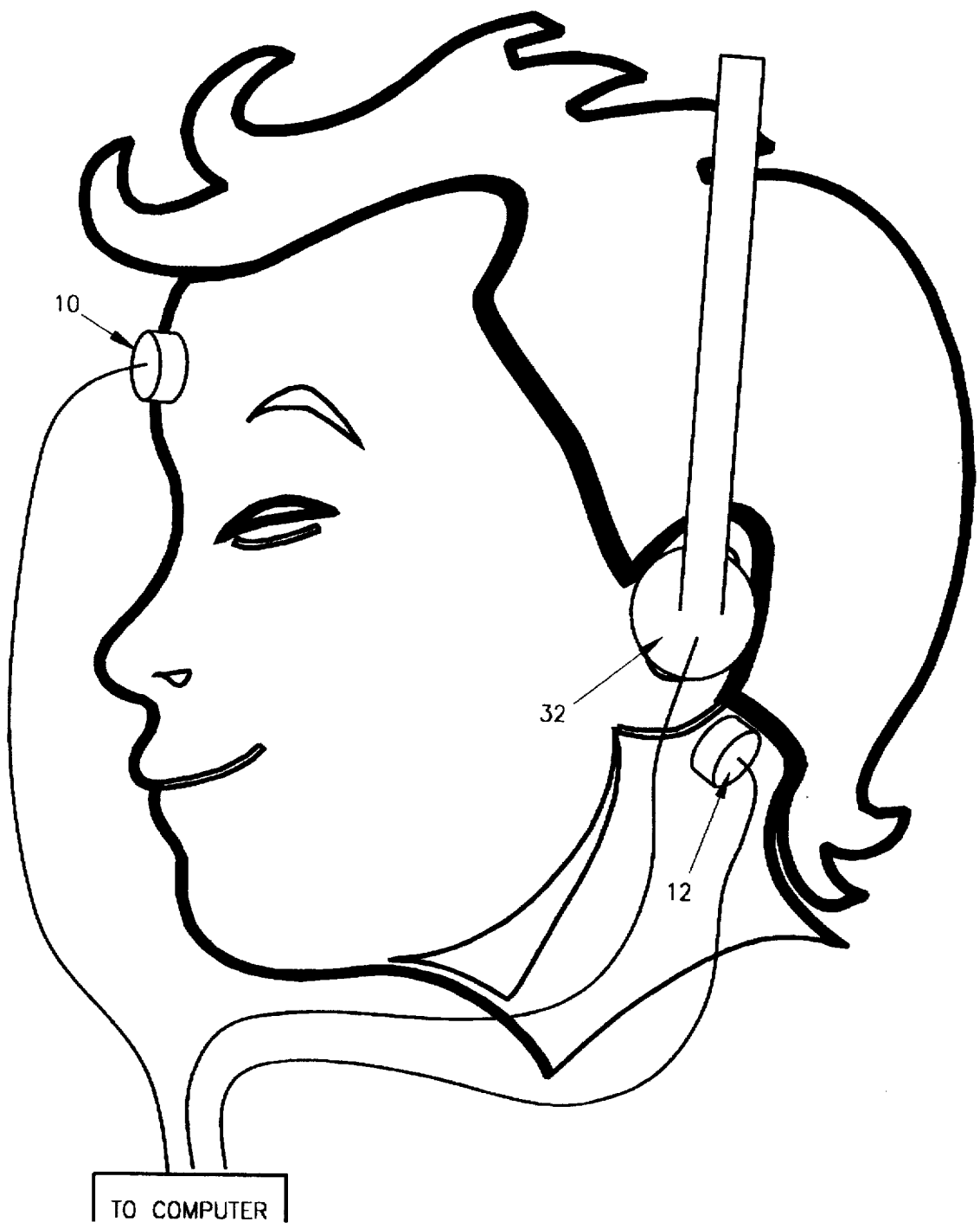
FIG. 16 is side view of a baby's head showing preferred placement of the scalp electrodes at the mastoid and vertext regions and use of the earphones to transmit the hearing stimulus to the test subject.

The apparatus used for the ABR testing method of the present invention is illustrated in FIG. 1 and the environment in which the tests were conducted is illustrated in FIG. 15. The apparatus comprises earphone 32 and scalp electrodes 10 and 12 which are connected to the vertex and mastoid regions of the head. A more detailed illustration of the placement of the electrodes and earphone is shown in FIG. 16. It should be noted that other regions may also be observed for neural ABR activity such as the C7 region. However, for the purposes of the present invention's testing and analysis, only the mastoid/vertex was used. Electrodes 10 and 12 are operative to detect and transmit neural activity as is well known in the art. Other suitable devices operative to transmit electrical pulses may also be used. In the preferred embodiment, Orthodynamics neonatal probes were used as earphones but other suitable earphones may be used. The neural activity detected by scalp electrodes 10 and 12 is amplified by OpAmps 14 and 16. The amplifiers are Opto-isolated to protect the test subject from any stray voltages. In the preferred embodiment, OpAmps 14 and 16 are Intelligent Hearing Systems Opti-Amp 2000 evoked potential (EP) amplifiers but other suitable alternatives are available. The amplified signals from OpAmps 14 and 16 are then transmitted to interface board 30 which is an analog-to-digital converter (ADC) and then to digital signal processing board 18. In the preferred embodiment, DSP board 18 is an Ariel DSP-16+I/O card adapted to be received in a personal computer but many suitable alternatives exist. In the preferred embodiment DSP 18, ADC 30, and DAC 34 (discussed below) are all adapted to fit on a computer board 44 for interfacing. The purpose of the DSP board 18 is to provide a means for digitally sampling the neural signal picked up by electrodes 10 and 12. The DSP board is adapted to be controlled by software, discussed below. The sampled neural signal is then transmitted to computer 20 for analysis. In the preferred embodiment, computer 20 is a personal computer but could be any of a number of computers either designed specifically to analyze ABR data or a general purpose computer programmed to accomplish this task.

Computer 20 provides a means for receiving and for processing the ABR data such as controlling the sampling and storing of the ABR data, subdividing the data into sweeps and blocks, forming the concurrent replication, and otherwise analyzing the data as described herein by computing the various averages and ratios. It will be understood by those in the art that these tasks may be accomplished in software and/or delegated to discreet components such as allowing the DSP 18 to control sampling or processors pre-programmed to perform these functions. The computer 20 of the present invention may have connected thereto conventional peripherals such as monitor 22, printer 28, memory 26, and keyboard 24.

The audio stimulus may be generated by any number of devices but in the present invention for ABR testing was generated by a digital-to-analog converter (DAC) which is also controlled by DSP board 18. It is important that the DAC and ADC be precisely synchronized in order to realize a benefit in signal-to-noise ratio from averaging repeated stimulus responses. In the present test method, the audio stimulus from the DAC 34 was a "click" comprising a 100 microsecond rectangular pulse calibrated to produce a 30 dB nHL peak (rarefaction) pressure in a reduced-volume HA-1 acoustic cavity. (The units "dB nHL" indicate decibels re normal adult thresholds. The 30 dB nHL stimulus was calibrated to have peak sound pressure level of 65 dB pSPL which is equivalent to 35.6 millipascal.) In the preferred embodiment, the audio stimulus was transmitted to the testing subject by means of earphones 32 but there could be any number of alternatives for transmitting audio signals.

The DSP board was programmed by the software to use a 50 kHz sample rate for both stimulus generation and ABR recording. As mentioned, only the recording of the electrical potential from vertex/C7 to mastoid was used in the analyses discussed herein.

Figure 2A:
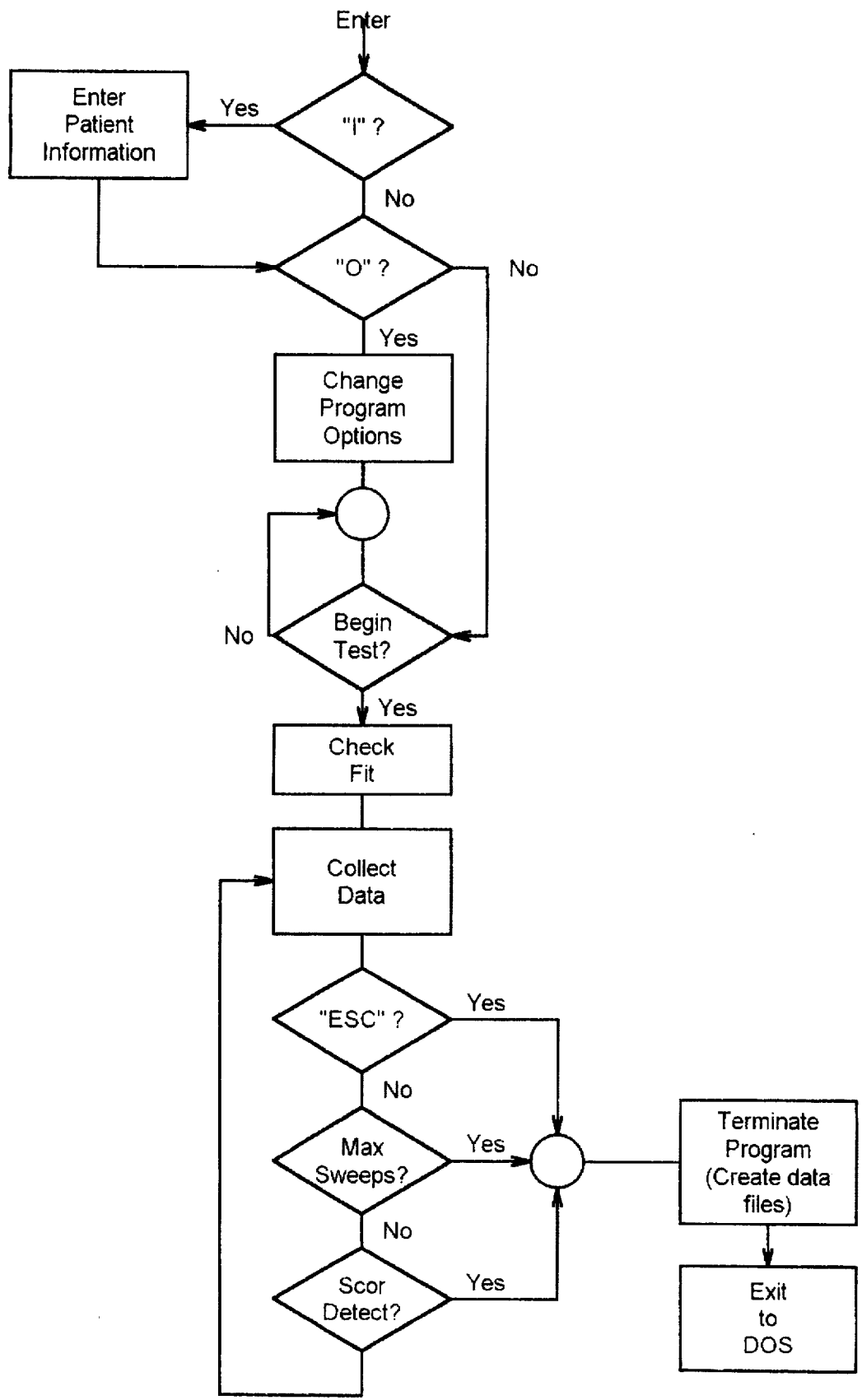
FIGS. 2a-b are a flow chart of the computer routine used to implement the analysis of the ABR test data according to the method of the present invention.
Figure 2B:
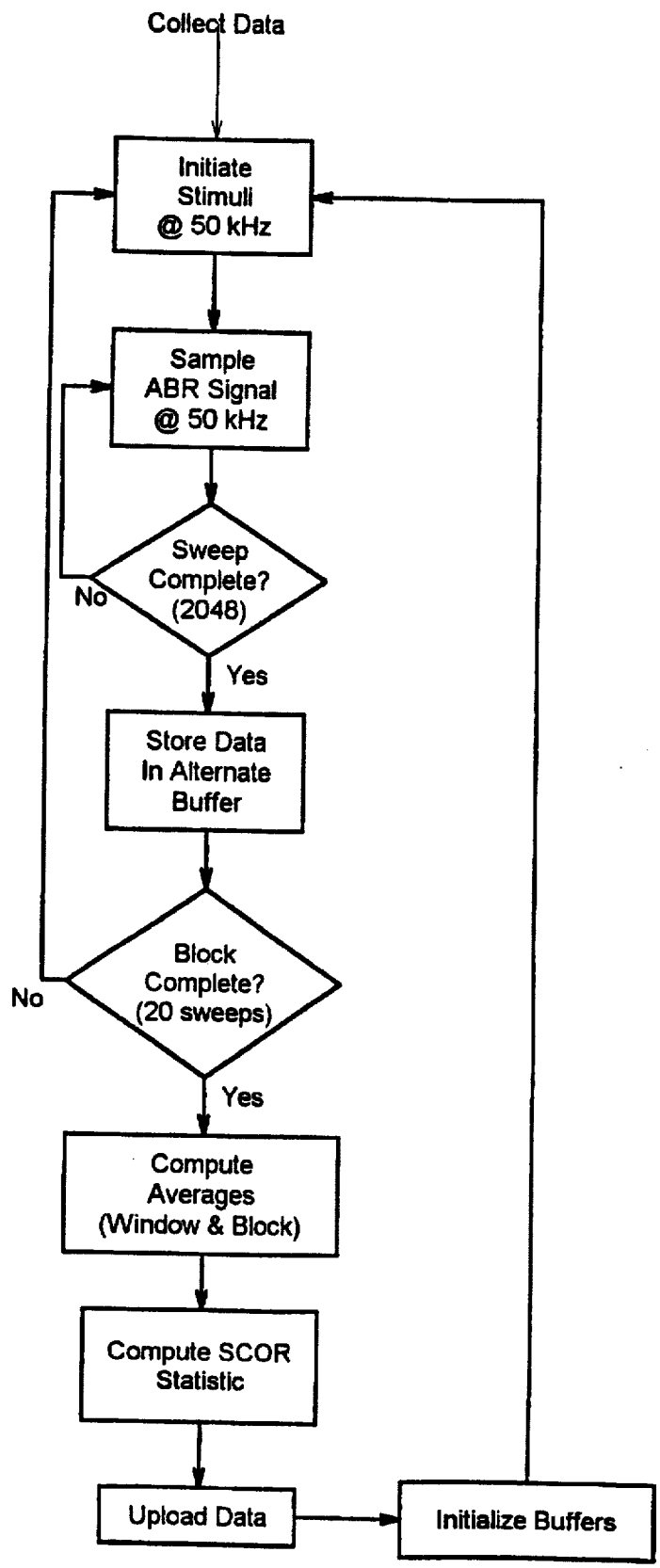

The novel computer routine utilized to implement the analysis of the present invention is designated the Auditory Brainstem Response Averager (ABRAV). FIGS. 2a–b illustrate a simple flowchart of the computer routine used to conduct the analysis of the test data according to the present invention. ABRAV is a routine for measuring and displaying auditory brainstem response data on a PC compatible computer. ABRAV works with same hardware described above. ABRAV has the ability to record and display two channels of evoked potential such as vertex/mastoid (36a and 36b) and vertex C7 (37a and 37b) although only the vertex/mastoid data is used here for analysis. Recording of ABR sweeps alternates between two separate buffers for each channel, effectively obtaining a replication of the waveform at the same time as the initial waveform. This novel feature is designated "concurrent replication." FIG. 12a illustrates the display of concurrently replicated waveforms 36a, 36b from the mastoid region. The purpose behind the concurrent replication feature is to provide the observer with a means for comparing sweeps, facilitating the discovery of any discrepancies or discontinuities therebetween in "real time" as the test proceeds. For example, the peaks indicated by I, III, and V correspond well between the two, replicated waveforms 36a and 36b, indicating valid ABR data. Additionally, concurrent replication may be used to facilitate statistical analysis of the ABR data. For example, the concurrent replication is used to compute the reproduceability factor from the cross-correlation between the two concurrently replicated waveforms. While the concurrent replication is helpful in determining signal validity, it is not necessary in computing the SCOR statistic. The signal to noise statistic (SCOR) 38 is calculated and displayed on monitor 22 during data collection. The operator can also manipulate the waveforms and mark peaks during data collection. Data files can be reviewed on a PC without the additional I/O hardware. These files can be redisplayed and printed to a printer 28.

The program is flexible enough to allow many different test parameters to be easily changed and is sufficiently "user friendly" to be used routinely in a clinical setting.

As mentioned, ABRAV has the ability to record two channels of evoked potential and display the average of sweeps on the screen. The accumulating of sweeps from each channel is alternated every 20 sweeps between two sets of buffers, so that two independent averages are maintained. Each group of 20 sweeps is referred to as a "block" and the averages as a "block average" (e.g. eg. 8). All waveforms may be shown on the screen, giving the appearance of obtaining a concurrent waveform replication simultaneously with the initial average. A reproduceability factor may be defined as the cross-correlation between the replicated waveforms.

In addition, signal statistics such as the FSP and SCOR statistic may be calculated and shown (both numerically 39 and graphically 38) on the screen (FIG. 12a). In conjunction with the SCOR statistic (38), the ABRAV will display when the SCOR value has crossed (point 42) the detection threshold (line 40) identified with good hearing. As mentioned, the numerical value of the threshold will shift depending on the signal processing performed on the ABR data. The program also has features to help with development of the ABR test. The most useful of these features is the ability to record and playback the raw data. This allows one to see the effect of performing the test with different parameters. The program allows changing many test parameters (such as type of weighing used for the average, digital high-pass and low-pass filters, and time-windows for the quality measures) through menu options. As mentioned, this may shift the SCOR threshold up or down. The default values for these parameters can be specified in a configuration file.

While a flow chart for a computer routine to embody the method and apparatus of the present invention has been illustrated, it will be clear to those in the art that many different modifications and alternatives are available which will implement the invention.

Tests were conducted to analyze the prior art methods of ABR data analysis as well as to develop the present invention. The responses to 4000 stimuli were recorded in blocks of 20 sweeps. Each sweep contained 2048 sample values at 20 microsecond intervals spanning a 41 msec time window post-stimulus. The sweep repetition rate was 24.4 sweeps/second within each block of 20 sweeps. An additional 78 msec time interval elapsed between blocks to allow for uploading of data to computer 20. For each block, data stored on computer 20 consisted of the block average for each of the 2048 sample values, along with the 20 single point values at 18.5 msec from the start of each sweep in the block. OpAmps 14 and 16 have a gain of 200,000 and the analog-to-digital converter (ADC) 30 converts ±10 volts to 16-bit integers. Thus, each unit of the ADC 30 values corresponds to about 1.5 nanovolts between the EP electrodes.

Of primary interest was the stored vector of 4000 data values, one for each sweep, at the single point 18.5 msec post-stimulus. From these data the residual noise in the averaged waveform was estimated for that point and this presumably reflected the residual noise at all points in the waveform.

Tests were conducted on 14 babies between 33 and 51 weeks conceptual age (28 and 42 gestational age). These babies were selected as subjects for the Identification of Neonatal Hearing project, a multicenter study sponsored by the National Institute on Deafness and Communication Disorders. The following data were obtained after the main study protocol had been completed for each baby. For ABR recording, babies were in open cribs, in a quiet but not sound-treated room and were generally sleeping. All babies were on battery powered monitors during the testing. Electrodes were placed at both mastoids, at the vertex and at the C7 regions of the head, although only the mastoid/vertex data is discussed herein.

b. Noise Estimates

Consider a single point relative to the start of each sweep an let $s_k$ denote the value at that point in the $k^{th}$ sweep. The time dependence is suppressed since only a fixed point in time is being considered. An estimate of the evoked potential $\mu$ at this point is represented by $$\bar{s} = \sum_{k=1}^{N} \frac{s_k}{N},$$

where N denotes the number of sweeps available. The residual noise in the average is the variance of this average $$RN = var(\bar{s}) = \frac{1}{N^2} var\left( \sum_{k=1}^{N} s_k \right) = \qquad (1)$$

$$\frac{1}{N^2} \left\{ \sum_{k=1}^{N} var(s_k) + \sum_{k=1}^{n} \sum_{j \neq k} cov(s_k, s_j) \right\},$$

where $$cov(s_k, s_j) = E[(s_k - \mu)(s_j - \mu)].$$

If the noise contribution to $\{s_k\}$ is stationary, and let $var(s_k) = \sigma^2$ and $cov(s_k, s_{k+i}) = \sigma^2(i)$, then the residual noise expression (1) can be rewritten as $$\text{var}(\bar{s}) = \frac{\sigma^2}{N} \left\{ 1 + 2 \sum_{i=1}^{N} \left(1 - \frac{i}{N}\right) \frac{\sigma^2(i)}{\sigma^2} \right\} = \quad (2)$$

$$\frac{\sigma^2}{N} \left\{ 1 + 2 \sum_{i=1}^{n} \left(1 - \frac{I}{n}\right) \rho(I) \right\}.$$

The quantity $$\rho(i) = \frac{\sigma^2(i)}{\sigma^2}$$

called the $i^{th}$ term in the autocorrelation sequence. This quantity indicates the strength of association between single point data values separated by i sweeps. It lies in the range [−1,1] with values of −1 and 1 indicating maximal association. If the single point values are independent of each other, the $\sigma(i)=0$ for all i.

The usual prior art single point estimate of the residual noise is based on the assumption of independence amongst sweeps, so that the autocorrelations are zero. Hence, the second term in Equation 2 would vanish and $$RN = \frac{\sigma^2}{N}.$$

An approximately unbiased estimate of $\sigma^2$ is the mean sum of squares, $$\sum_{k=1}^{N} \frac{(s_k - \bar{s})^2}{N}.$$

This is denoted by var(SP) and the resultant estimate of the residual noise is the mean sum of squares (mss) estimator $$RN_{mss} = \frac{1}{N} \left\{ \sum_{K=1}^{N} \frac{(s_K - \bar{s})^2}{N} \right\}. \quad (3)$$

The data below, however, indicate that sweeps cannot be assumed to be independent because the autocorrelations $\rho(i)$ are non-zero. Hence, the estimator $RN_{mss}$ is a biased estimate of the residual noise which would lead to an improper analysis of the ABR waveform. To reduce the effect of this bias, one strategy is to estimate the autocorrelation sequence from the data with $$\hat{\rho}(i) = \frac{\sum_{k=1}^{N-i} \frac{(s_k - \bar{s})(s_{k+i} - \bar{s})}{N-i}}{\sum_{k=1}^{N} \frac{(s_k - \bar{s})^2}{N}}, \quad (4)$$

and to substitute these $\hat{\rho}(i)$, along with an estimate of $\sigma^2$ into Equation 2. The resulting expression for the residual noise estimate is $$RN_c = RN_{mss} \left\{ 1 + 2 \sum_{i=1}^{N} \left(1 - \frac{i}{N}\right) \hat{\rho}(i) \right\}. \quad (5)$$

This is called the corrected mean sum of squares estimator (cmss). The factor in brackets in Equation 5 corrects the $RN_{mss}$ estimate for possible dependence among sweeps. In many instances, it will be reasonable to choose a number I such that $\rho(i)$ is negligible for $i>I$. That is, data points more than I sweeps apart may reasonably be regarded as uncorrelated. The corrected mean sum of squares then can be written as $$RN_c(I) = RN_{mss} \left\{ 1 + 2 \sum_{i=1}^{I} \left(1 - \frac{i}{N}\right) \hat{\rho}(i) \right\}. \quad (6)$$

and this is called the mean sum of squares corrected for dependence of order I. This estimate will be computationally more feasible in practice as I is likely to be much smaller than the number of sweeps N. It is also likely to be statistically more stable as fewer terms are to be estimated.

A simple alternative way to reduce the bias in $RN_{mss}$ due to correlations amongst sweeps is based on segmenting the single point values into consecutive blocks of equal size and computing means within each block. If blocks are of size B, the vector of N single point values is reduced to an $N_B=N/B$ vector of block means $\{\bar{s}_1, \ldots, \bar{s}_{N_B}\}$. If block sizes are reasonably large, and serial correlations decrease as the number of sweeps separating points increases, then block means are likely to be substantially less correlated than are data points in adjacent sweeps. Since the average waveform can be written as the average of block means, $$\bar{s} = \sum_{b=1}^{N_B} \frac{\bar{s}_b}{N_B},$$

and now assuming that block sizes are sufficiently large to render the block means approximately uncorrelated, the residual noise can be written as $$\text{var}(\bar{s}) = \frac{1}{N_B} \text{var}(\bar{s}_b), \quad (7)$$

which can be estimated with $$RN_{BM}(B) = \frac{1}{N_B} \left\{ \sum_{b=1}^{N_B} \frac{(S_b - \bar{S})^2}{N_B} \right\}. \quad (8)$$

This is called the block average estimator of the residual noise with blocks of size B. The block average estimator (Eq. 8) and the corrected mean sum of squares estimator (Eq. 6) provide better estimates of residual noise than the usual estimator (Eq. 3) when sweeps are dependent. The following examines the extent of intersweep dependence in the test data.

c. Noise Estimate Test Results

Figure 3A:
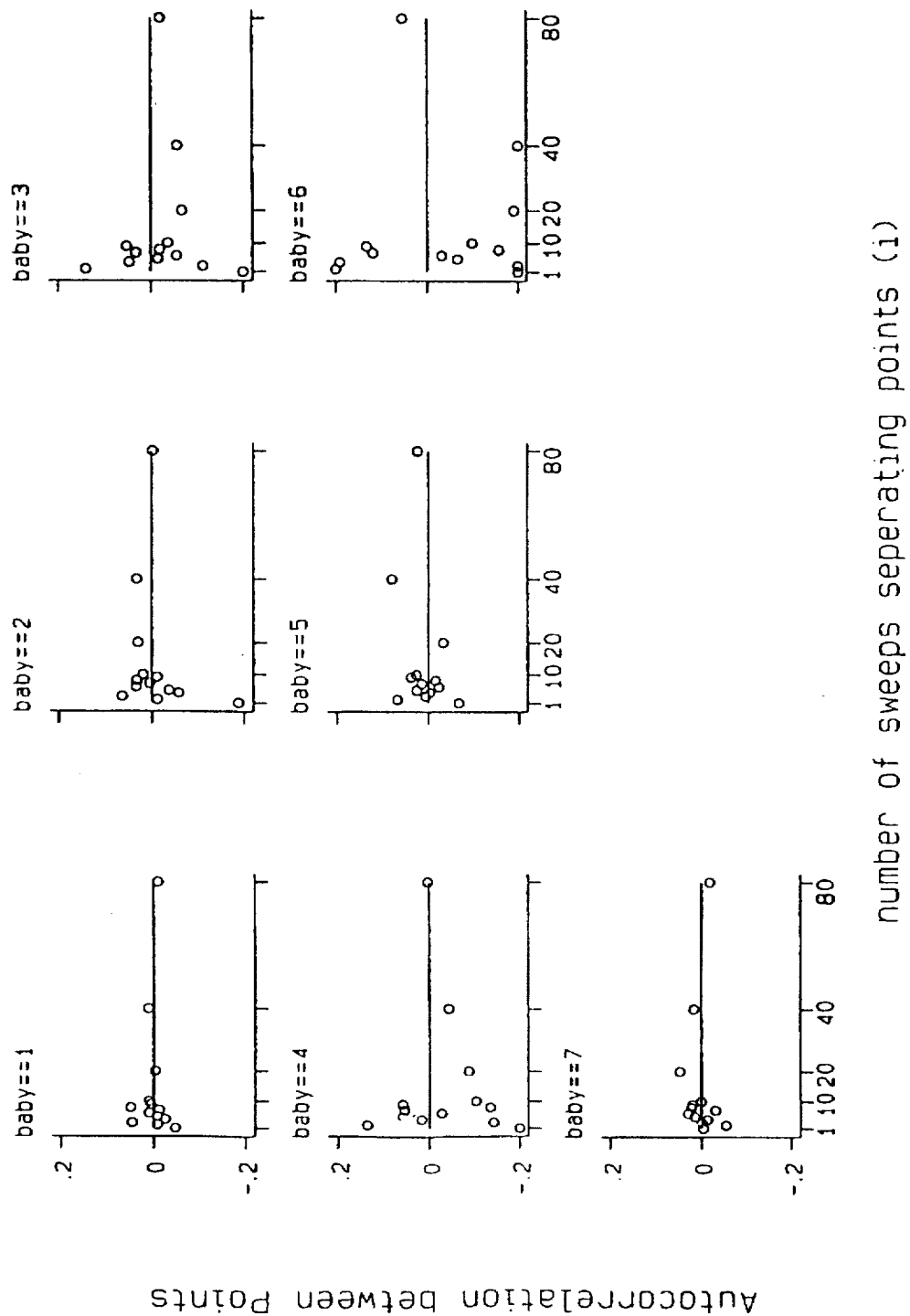
FIGS. 3a and b are graphs illustrating the autocorrelation between data points as a function of the number of sweeps in the test data utilizing prior art analysis methods.
Figure 3B:
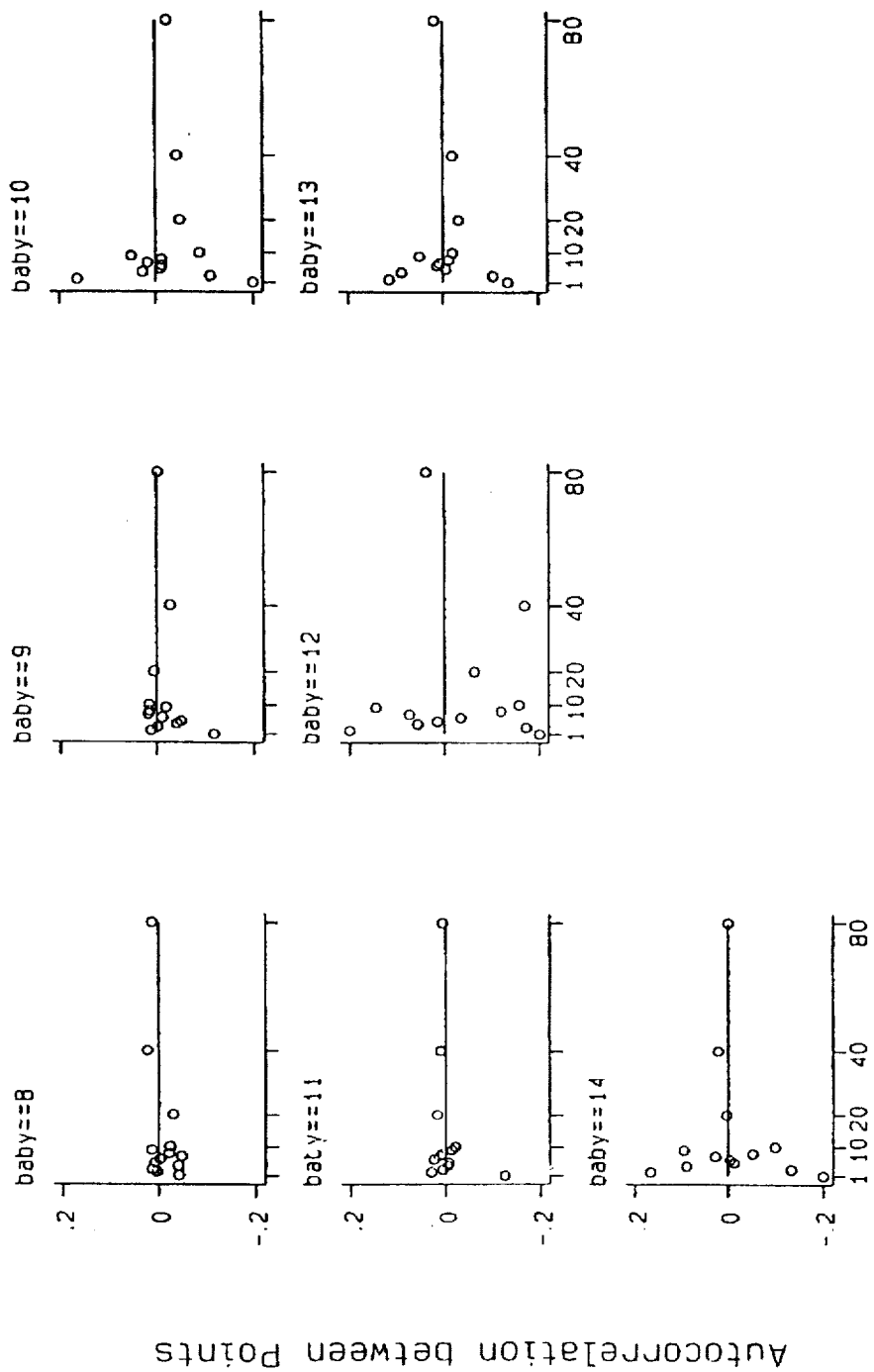
FIGS. 3-6 relate to test data taken in conjunction with prior art methods.
Figure 4:
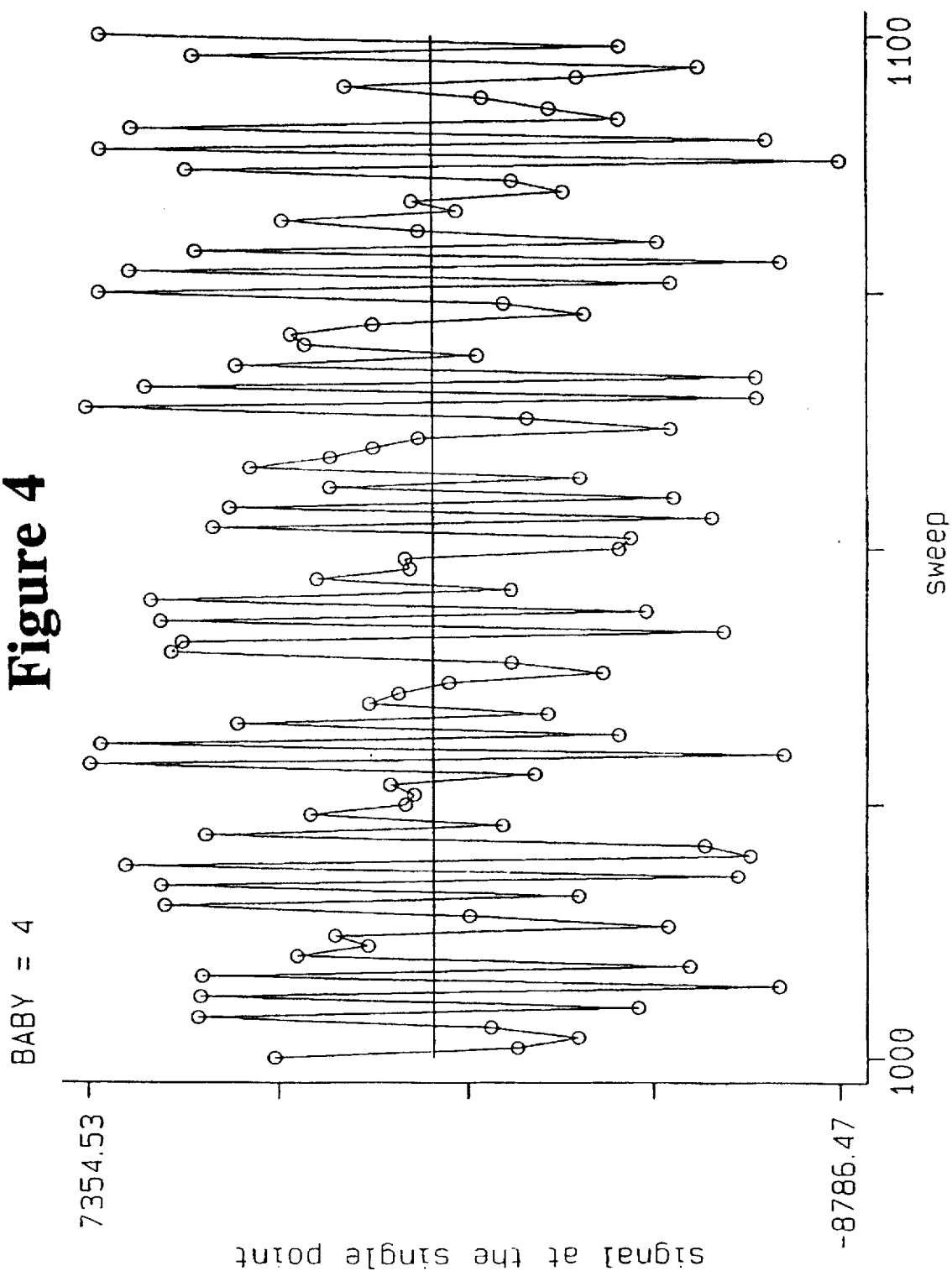
Figure 5:
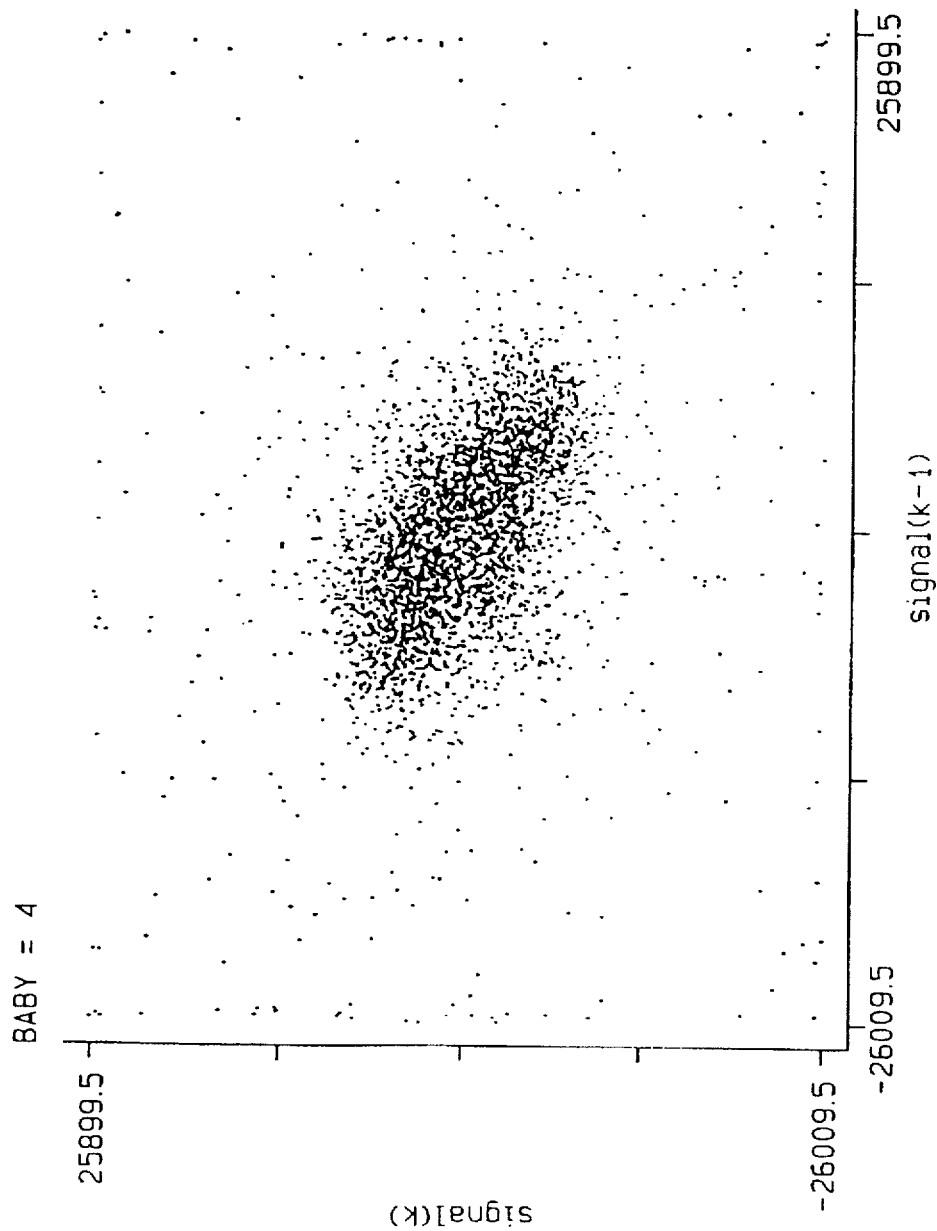

For each of the 14 babies in the test, the correlation between single point values i sweeps apart were calculated for i=1, 2, 3 . . . 8, 9, 10, 20, 40 and 80. These autocorrelations were calculated using equation (4) and are displayed as a function of the number of sweeps in FIGS. 3a and b. As seen in the figures, the results suggest that for most babies, data points separated by fewer sweeps are more strongly correlated than those separated by a larger number of sweeps. The autocorrelations with the first adjacent sweep, $\rho(1)$ were negative in all cases and statistically significant (p<0.01) in 13 of the 14 babies. Values are displayed in Table 1. The negative correlation between consecutive sweeps suggests that values above the mean on one sweep tend to be followed by values below the mean on the next sweep. This oscillation for a single baby (baby 4) can be seen in FIG. 4 where the single point values for 100 sweeps are plotted in sequence. FIG. 5 displays a scattergram of values on one sweep plotted against values on the previous sweep for this same baby. Again, the strong negative correlation is obvious.

TABLE 1

Serial autocorrelations of single point values for i = 1, 2, 3, 20, 40, 80.
P-values* are shown in parentheses.

| Baby | \multicolumn{2}{c}{Number of Sweeps separating points (i)} | | | | | | | | | | |
|------|------|------|------|------|------|------|------|------|------|------|------|------|
|      | \multicolumn{2}{c}{1} | \multicolumn{2}{c}{2} | \multicolumn{2}{c}{3} | \multicolumn{2}{c}{20} | \multicolumn{2}{c}{40} | \multicolumn{2}{c}{80} |

| Baby | 1 | | 2 | | 3 | | 20 | | 40 | | 80 | |
|------|-----|-------|-----|-------|-----|-------|------|-------|------|-------|------|-------|
| 1  | −.05 | (<.01) | −.01 | (.59)  | .05  | (<.01) | −.004 | (.82)  | .011  | (.49)  | −.011 | (.50)  |
| 2  | −.19 | (<.01) | −.01 | (.46)  | .06  | (<.01) | .029  | (.07)  | .032  | (.05)  | −.004 | (.82)  |
| 3  | −.25 | (<.01) | .14  | (<.01) | −.11 | (<.01) | −.067 | (<.01) | −.057 | (<.01) | −.021 | (.19)  |
| 4  | −.32 | (<.01) | .14  | (<.01) | −.14 | (<.01) | −.087 | (<.01) | −.043 | (<.01) | .003  | (.87)  |
| 5  | −.07 | (<.01) | .07  | (<.01) | .01  | (.70)  | −.030 | (.04)  | .080  | (<.01) | .024  | (.13)  |
| 6  | −.64 | (<.01) | .44  | (<.01) | 0.33 | (<.01) | −.192 | (<.01) | −.269 | (<.01) | .054  | (<.01) |
| 7  | −.01 | (.73)  | −.05 | (<.01) | −.00 | (.91)  | .046  | (<.01) | .016  | (.32)  | −.020 | (.22)  |
| 8  | −.04 | (<.01) | .00  | (.89)  | .01  | (.46)  | −.029 | (.06)  | .023  | (.15)  | .013  | (.42)  |
| 9  | −.12 | (<.01) | .01  | (.46)  | −.00 | (.92)  | .005  | (.77)  | −.029 | (.07)  | −.004 | (.81)  |
| 10 | −.34 | (<.01) | .16  | (<.01) | −.11 | (<.01) | −.050 | (<.01) | −.041 | (.01)  | −.024 | (.13)  |
| 11 | −.13 | (<.01) | .03  | (.05)  | .01  | (.68)  | .017  | (.28)  | .010  | (.52)  | .006  | (.69)  |
| 12 | −.52 | (<.01) | .32  | (<.01) | −.17 | (<.01) | −.063 | (<.01) | −.168 | (<.01) | .038  | (.02)  |
| 13 | −.14 | (<.01) | .11  | (<.01) | −.11 | (<.01) | −.033 | (.03)  | −.020 | (.20)  | .017  | (.27)  |
| 14 | −.29 | (<.01) | .17  | (<.01) | −.13 | (<.01) | .003  | (.84)  | .020  | (.21)  | −.001 | (.96)  |

*Calculated using a simple linear regression of $(S_k - \bar{S})$ on $(S_{k-i} - \bar{S})$.

Other terms in the autocorrelation sequence were also non-zero. Whenever the first term in the sequence had a large negative value the second term would tend to be positive, as would be expected from the pattern of oscillation seen in FIG. 4. Beyond that, however, the only consistency across babies is that the correlations tend to decrease as the number of sweeps i separating the data points increases with the largest correlation for i=1. Correlations at i=40 were small, but significantly different from zero in 7 of the 14 babies. At i=80 correlations were statistically significant in only two babies (babies 6 and 12).

The analyses described above demonstrate that there is considerable dependence amongst data points obtained relatively close in time. Thus, the independence assumption upon which the usual residual noise estimate relies ($RN_{mss}$) does not hold. The violation of this assumption impacts the mean sum of squares estimator $RN_{mss}$ and consequently any conclusions regarding the ABR analyzed with this noise estimator.

Figure 6A:
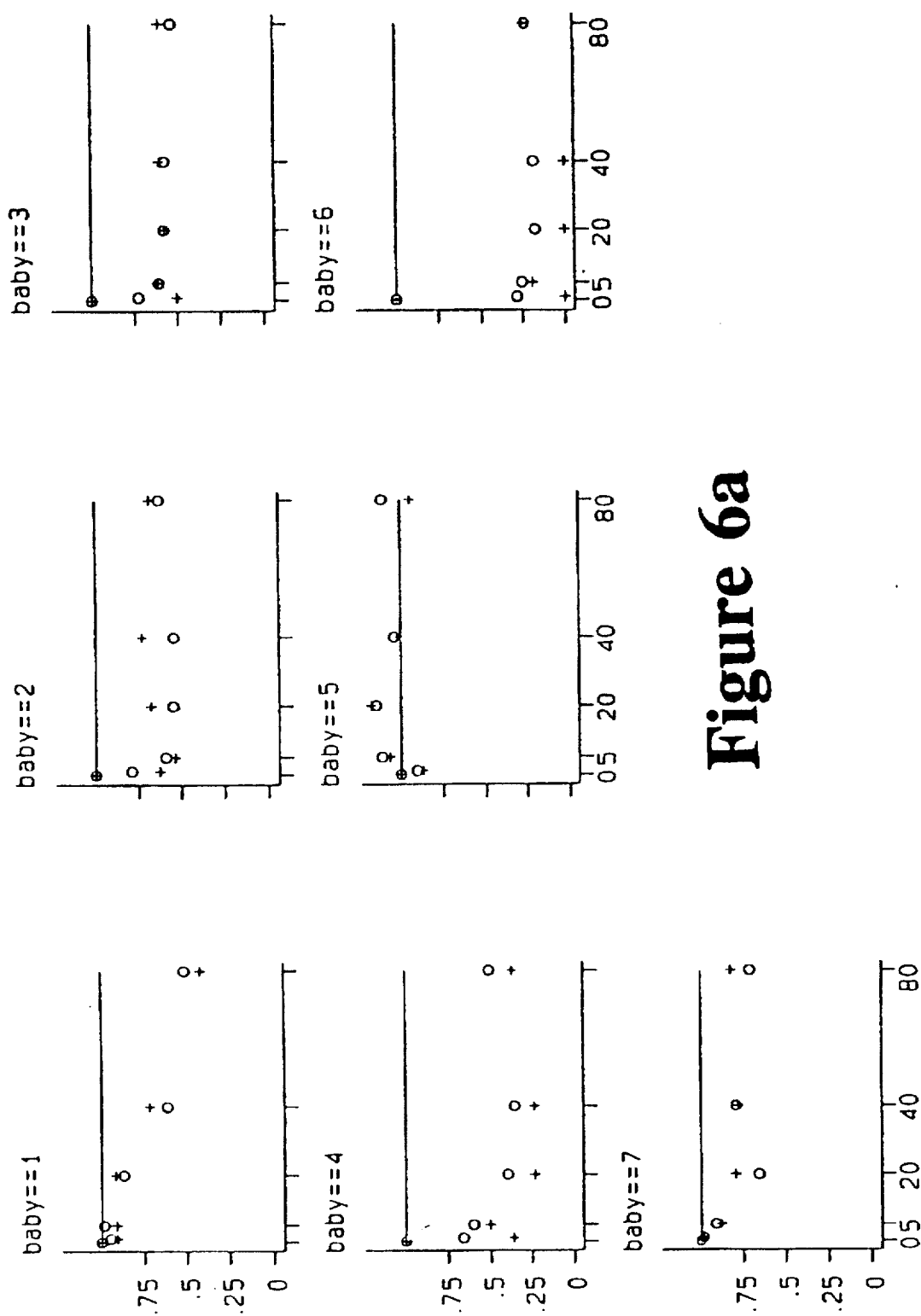
FIGS. 6a and b are graphs illustrating the residual noise estimate/usual estimate as a function of sweep number.
Figure 6B:
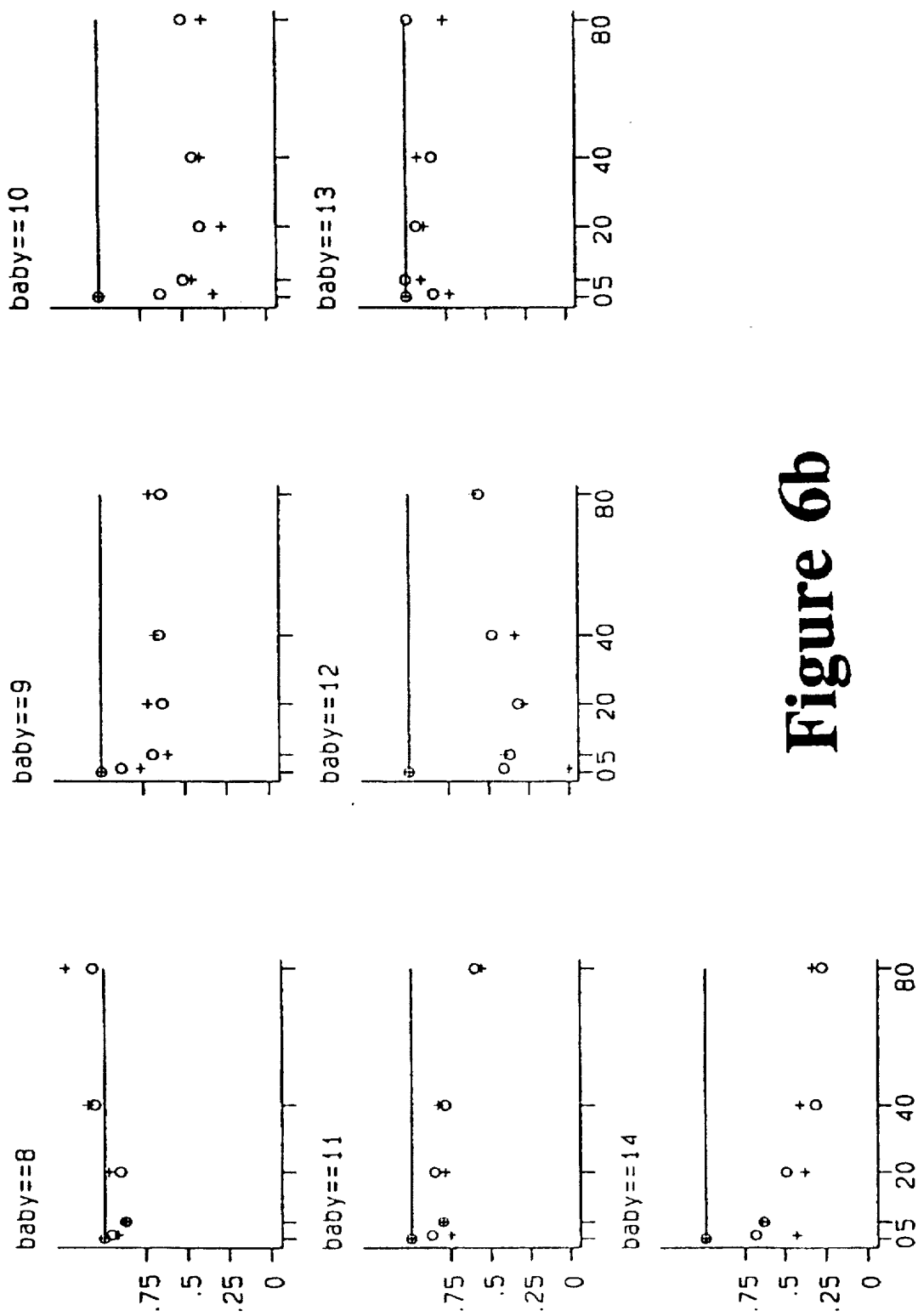

For each baby the corrected mean sum of squares estimate $RN_c(I)$ was compared to the uncorrected value $RN_{mss}$ for various levels of correction. The ratio of these estimates $$\frac{RN_c(I)}{RN_{mss}}$$

is displayed in FIGS. 6a and b for I=0, 1, 5, 20, 40, and 80. Observe that at I=0 there is no correction; hence the ratio $$\frac{RN_c(0)}{RN_{mss}} = 1.$$

Analyses of the autocorrelations suggested that they were negligible for I>80. Therefore, the residual noise estimate correcting for I=80 is regarded as unbiased. FIGS. 6a and b shows that the correction significantly decreased the estimate of the residual noise in comparison to the value estimated by the usual method. In other words, the usual estimate tends to provide an overestimate of the amount of residual noise.

Also shown in FIGS. 6a and b are the block average variance estimates, again displayed as a ratio relative to the usual variance estimate. For each value of I, the block size was taken as 2I, so the displayed values are $$\frac{RN_{BM}(2I)}{RN_{mss}}.$$

The amount of correction achieved by $RN_{BM}$ relative to the block size depends strongly on the type of autocorrelation in the data. Therefore, the interpretation for $RN_{BM}$ as correcting for a given number of autocorrelation is not as straightforward as it is for $RN_c(I)$. In FIGS. 6a and b, $RN_c(II)/RN_{mss}$ was plotted against I simply because the average distance between single points in adjacent blocks is then approximately I. The plot demonstrates that the block average variance estimates are also significantly smaller than the usual variance estimate for most babies. This is further evidence that the usual estimate is biased in the data and provides an overestimate of the residual noise. At I=80 the block mean and corrected estimators agree rather closely.

The above results suggest that the usual estimate of the residual noise is biased, but are not definitive since the true residual noise is unknown in each case. Only estimates of it are available to be compared with each other. Computer simulations in which data were repeatedly generated from a statistical model allow a calculation of the true residual noise of the average waveform for the data from the model and an evaluation of the various estimates of it.

The model was developed to mimic data from one of the babies (baby 4). The model, which is termed an autoregressive model in statistical literature or linear prediction model in speech analysis literature, is a linear regression model of the single point data $s_k$ as predicted by prior data points. The model which fit the data from baby 4 is $$s_k = \sum_{j=1}^{5} \alpha_j s_{k-j} + \epsilon_k, \quad (9)$$

where the terms $\epsilon_k$ have mean zero. The estimated parameters were $\alpha_1=-0.306$, $\alpha_2=0.017$, $\alpha_3=0.118$, $\alpha_4=0.04$, and $\alpha_5=0.069$, and the standard deviation of $\epsilon_k$ was estimated to be 5737.5.

In each simulation, a data set of 4000 single point values was generated from this model (9) with $\epsilon_k$ normally distributed using the parameters described above. The first 5 values were calculated assuming sj=0 for j≤0. Simulated data points from the model have mean 0 and have variance and autocorrelations similar to the single point values for baby 4.

One-thousand simulated data sets were generated. For each data set, the mean $\bar{s}$ and the residual noise estimates $RN_{mss}$, $RN_c(I)$, and $RN_{BM}(2I)$ were calculated for I=1, 5, 20, 40, and 80. The true residual noise var($\bar{s}$) was calculated as the variance of $\underline{s}$, over the 1000 data sets and was found to be RN=5994. This is, by definition, the residual noise in $\bar{s}$, the average. Table 2 summarizes the estimates of this quantity obtained in the simulated data sets. The usual estimate produced values in the range 9365±492 in 95% of the data sets. Clearly this estimate is biased too large, being substantially larger than the true residual noise value of 5994. On the other hand, the estimates which account for the dependence among the data points are much closer to the true residual noise. The corrected mean sum of squares estimate (Eq. 6) provided good estimates even with I=5. The block average estimator (Eq. 8) required segmenting the data into blocks of 40 or more to yield valid estimates of residual noise.

normally distributed which has certain statistical advantages. For example, a confidence interval for RN can be obtained from $RN_{BM}$ using the fact that $$N_b \times \frac{RN_{BM}}{RN}$$

has a chi-squared distribution with $N_B-1$ degrees of freedom.

Another issue is the non-stationarity of the noise. Bursts of noise do occur. Previous studies have suggested weighing the data within blocks by the inverse of the mean of the sum of squares within each block. This may improve the stationarity of the noise, although, weighing by the square root of this quantity would seem to be more appropriate if the objective is to improve stationarity. Such weighing has been investigated and did not alter any of the conclusions discussed above.

TABLE 2

Estimates of residual noise from 1000 data sets with each data set generated by a computer from a statistical model based on data from baby number 4. The true residual noise is 5994. Displayed are mean estimates and standard deviation in parentheses. The usual estimate has a mean of 9365 (sd = 246).

|  | L | | | | |
|---|---|---|---|---|---|
|  | 1 | 5 | 20 | 40 | 80 |
| Corrected Estimate $RN_{mss}^c(L)$ | 10360 (405) | 5842 (597) | 6176 (956) | 6086 (1268) | 5914 (1733) |
| Block Average Estimate $RN_{BM}(2L)$ | 9866 (331) | 7835 (569) | 6645 (945) | 6417 (1284) | 6249 (1791) |

In the ABR test system, substantial autocorrelations among single point values were found which rendered invalid the usual method of estimating residual noise. The exact sources of these autocorrelations is unknown but clearly any noise nonuniformly distributed in frequency and which lasts for several sweeps can induce such correlation. Spectral analyses of the single point values were not entirely consistent across babies. However, they did indicate strong peaks at 10.7 and 11.8 Hz in several cases. The ever present 60 Hz line noise may have given rise to these double peaks. With constant sampling and exactly 41 msec between single points, 60 Hz noise would induce a spectral peak at 11.2 Hz. The sampling in the system was interrupted every 20 sweeps for 78 msec to upload data to the PC. The periodic gap in recording might have caused an 11.2 Hz peak in the spectrum to split into 2 peaks separated by 1.1 Hz. Other sources of noise including α and δ waves and muscle tension cold also conceivably contribute to the observed autocorrelations.

It will not usually be possible to eliminate all noise sources which induce correlations amongst single point values. Therefore estimates of residual noise need to account for possible non-independence of sweeps. It has been shown above that the corrected mean sum of squares estimate $RN_c$ (Eq. 6) and the block average estimate $RN_{BM}$ (Eq. 8) both have significantly less bias than the usual estimate $R_{Nmss}$ (Eq. 3). The block average method is preferred because it is computationally faster (an important consideration when it must be computed repeatedly during data collection) and conceptually easier. In the test data from babies, the corrected estimate actually gave negative values in some cases when an insufficient number of autocorrelations had been accounted for. Block averages are also more likely to be These results have important implications for objective detection of the ABR. Current detection algorithms based on a signal to noise ratio rely on good estimation of residual noise for the denominator component. The current mean sum of squares estimator of noise appears to be biased too large. This makes the signal-to-noise ratio biased too small, and hence the current detection method is less sensitive to the ABR signal than it ought to be. Since termination of the test is dependent on the signal detection method, increased test time is a consequence. Faster and more accurate detection, which is particularly important for large scale screening programs is achieved by replacing the usual estimate of residual noise in equation 8.

2. Signal to Noise Ratios

One conventional method for computing a signal-to-noise ratio to detect the ABR signal, is the FSP algorithm as follows:

$$FSP = \left\{ \sum_{i}^{m} (\bar{s}_i - \bar{\bar{s}})^2/M \right\} / \{VAR(SP)/N\}, \tag{10}$$

where i indexes a point in the time window, m is the number of such points, $\bar{s}_i$ is the average waveform at i and $\bar{\bar{s}}$ is the average $\bar{s}_i$ over the time window. Var(SP) is the variance of the single point values calculated in the usual fashion $$\sum_{}^{N} (S_{sp} - \bar{S}_{sp})^2/N$$

and N is the number of sweeps.

As can be seen from this equation, this FSP signal-to-noise ratio computation uses the prior art mean sum of squares estimator for the residual noise, illustrated in Equation 3 above. For an estimate of the signal, the FSP uses a computation of the summations of the variances of the signal data points within a time window. Results using this detection method are discussed below. Another method used to detect the presence of the ABR signal is the FMP algorithm.

$$FMP = \left\{ \sum_{i=1}^{m} (\bar{S}_i - \bar{s})^2/m \right\} /Ave\{RN_{BM}(100)/NB\} \quad (11)$$

The signal estimate used in the FMP algorithm will be observed as identical to that in the FSP algorithm. However, the estimate of the noise used in the FMP algorithm is the novel estimator described above in Equation 8. Results using this detection algorithm are also discussed below.

Another, and preferred, estimator is the SCOR estimator.

$$SCOR = FMP \times \Sigma(\mu_i - \bar{\mu})/\sqrt{\Sigma(\mu_i - \bar{\mu})^2 (s_i - \bar{s})^2} \quad (12)$$

In the preferred embodiment, the SCOR estimator uses the simple unweighted signal estimator and noise estimator from the FMP algorithm above in conjunction with the cross correlation between the observed data and a benchmark waveform template ($\mu$). The benchmark waveform template was prepared by averaging together ABR waveforms from a large number of normal hearing subjects. The template therefore provides a master against which future test data may be compared. Thus, the improved signal detection method of the present invention incorporates not only a vastly improved estimator for the noise component of the detection method but also compares this improved signal-to-noise estimator with a master template in order to arrive at an algorithm statistic which provides the test taker with a definitive quantitative indication of the hearing capacity of the tested subject. As mentioned, while preferred, concurrent replication is not necessary in computing the SCOR statistic.

As will be illustrated in more detail below, testing using the improved SCOR detection statistic of the present invention has shown that once the value of the statistic exceeds a predetermined value (Point 42 FIG. 12a), the hearing test may be concluded and the subject identified as having normal hearing.

3. Test Results Using The Improved Signal and Noise Estimators

The above three signal detection algorithms (FSP, FMP, and SCOR) were employed in another test of 50 babies. The test parameters were similar to those discussed above in connection with the development of the improved residual noise detection method illustrated in Equation 8. The babies were tested under 30 dB stimulus/no stimulus conditions. As with the analysis of the noise estimates above, the test data were taken from Channel A which indicates placement of the test electrode to the mastoid. Each block included 200 sweeps and a block size of 100 (B=100, Eq. 8) was used in determining the residual noise factor used in the signal-to-noise computation. Two different sized windows were used in computing the detection statistics, a 2–35 msec window and a 2–15 msec window.

Using data from 4000 sweeps under stimulus and no stimulus conditions each of these statistics was calculated. The 6 panels in each of FIGS. 7–9 display the 6 statistics with the upper row corresponding to the "no-stim" data and the lower row corresponding to the "stim" data. The plots were truncated at the median values for the no-stim and stim values, allowing us to see the display of values in the mid range.

Figure 7:
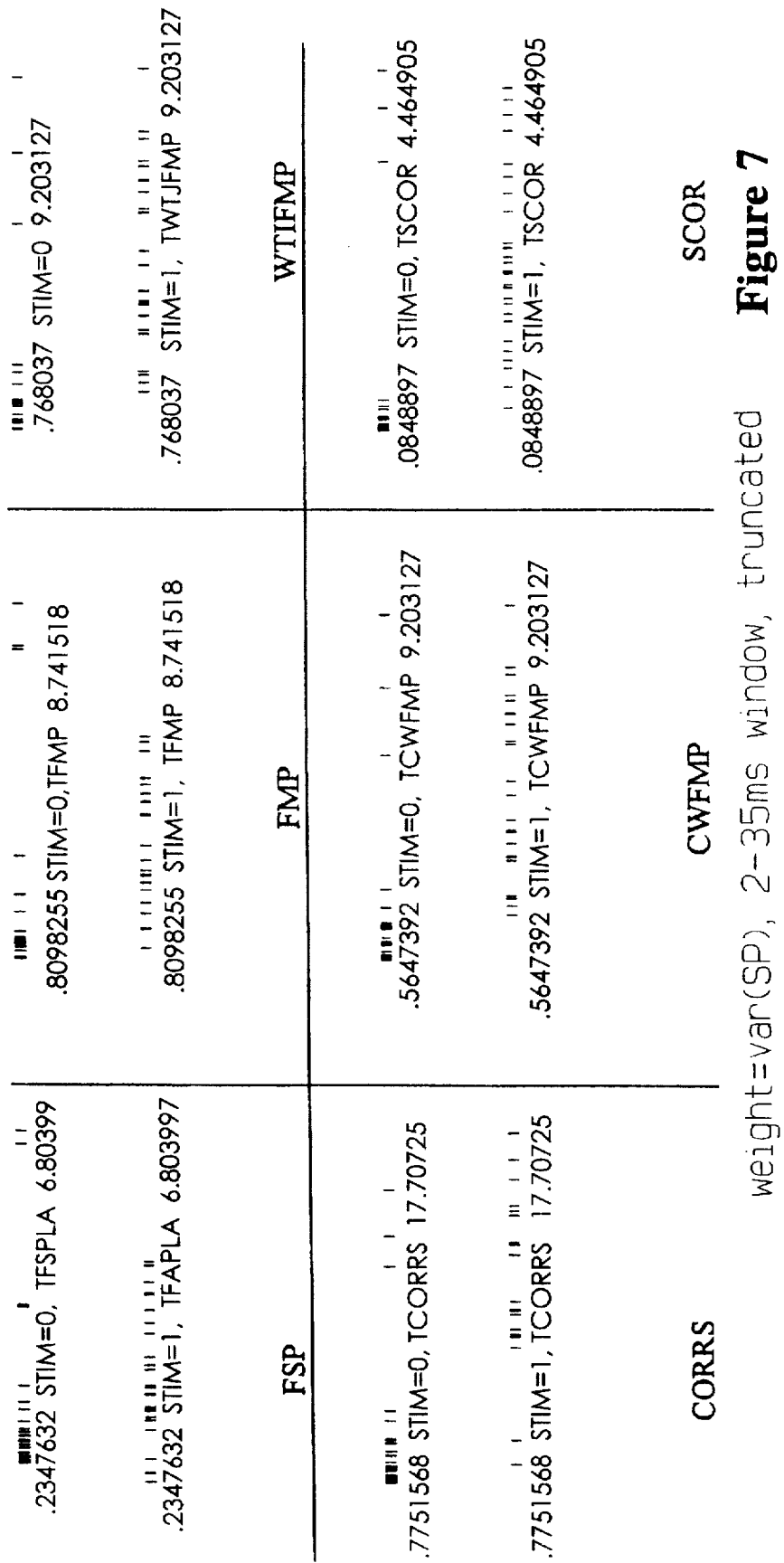
Figure 10:
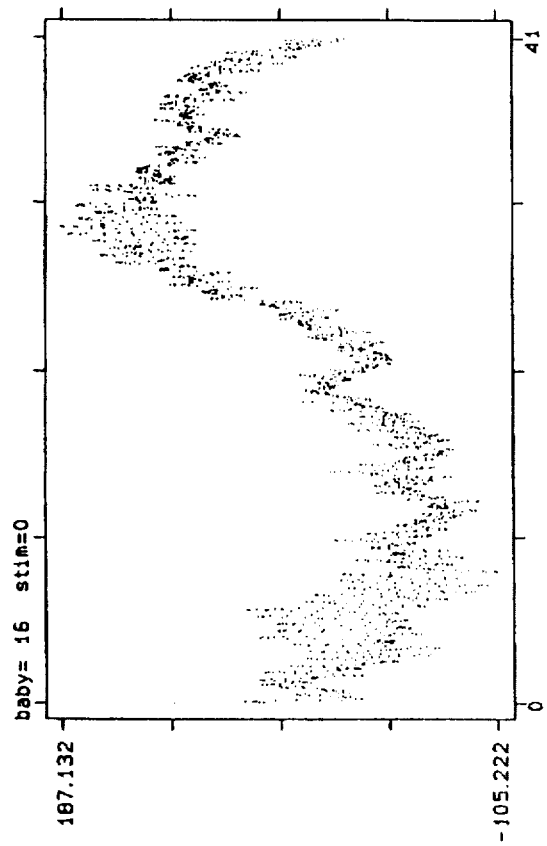
Figure 10:
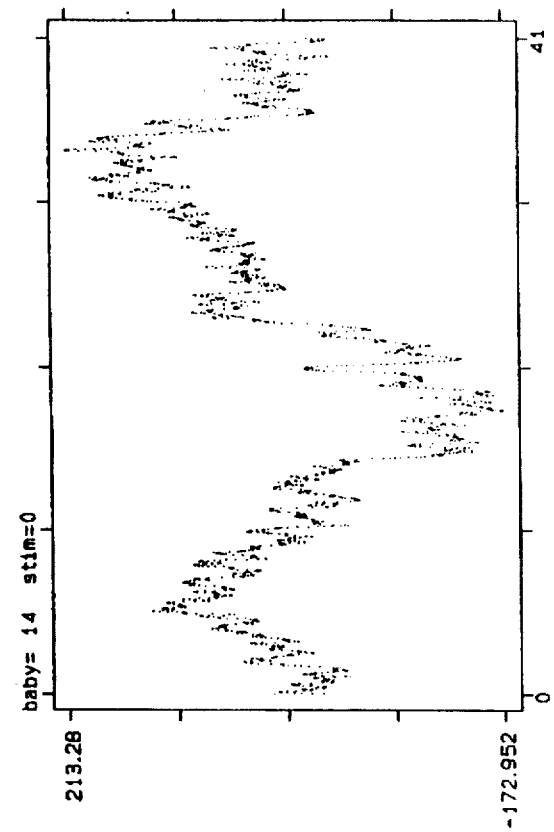
Figure 10:
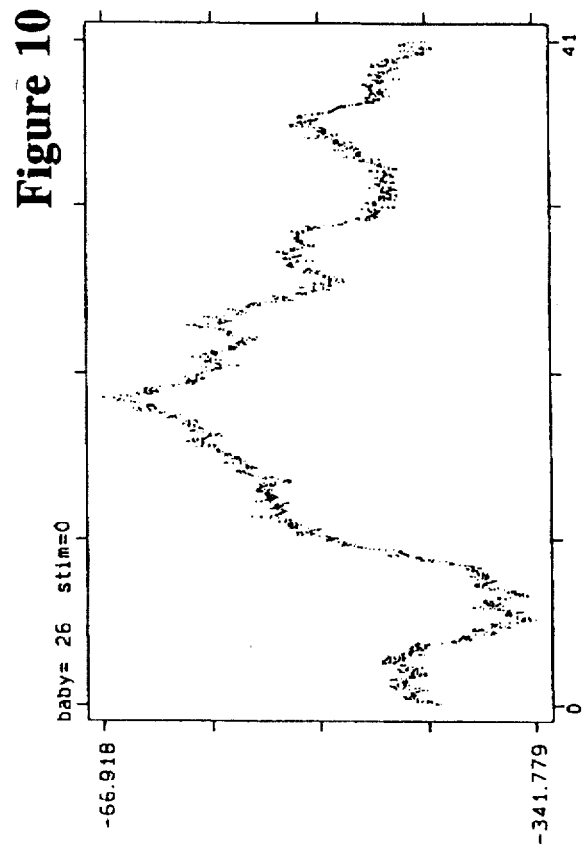
Figure 10:
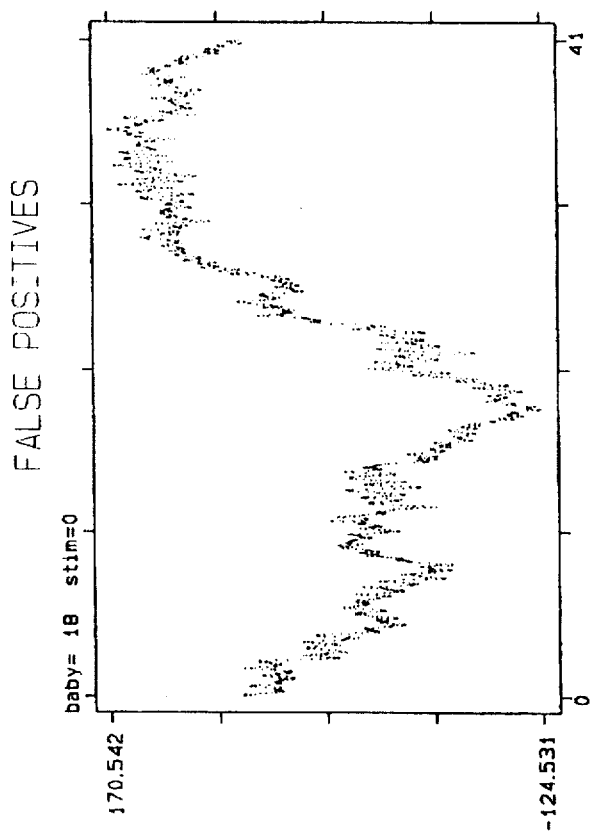
Figure 11:
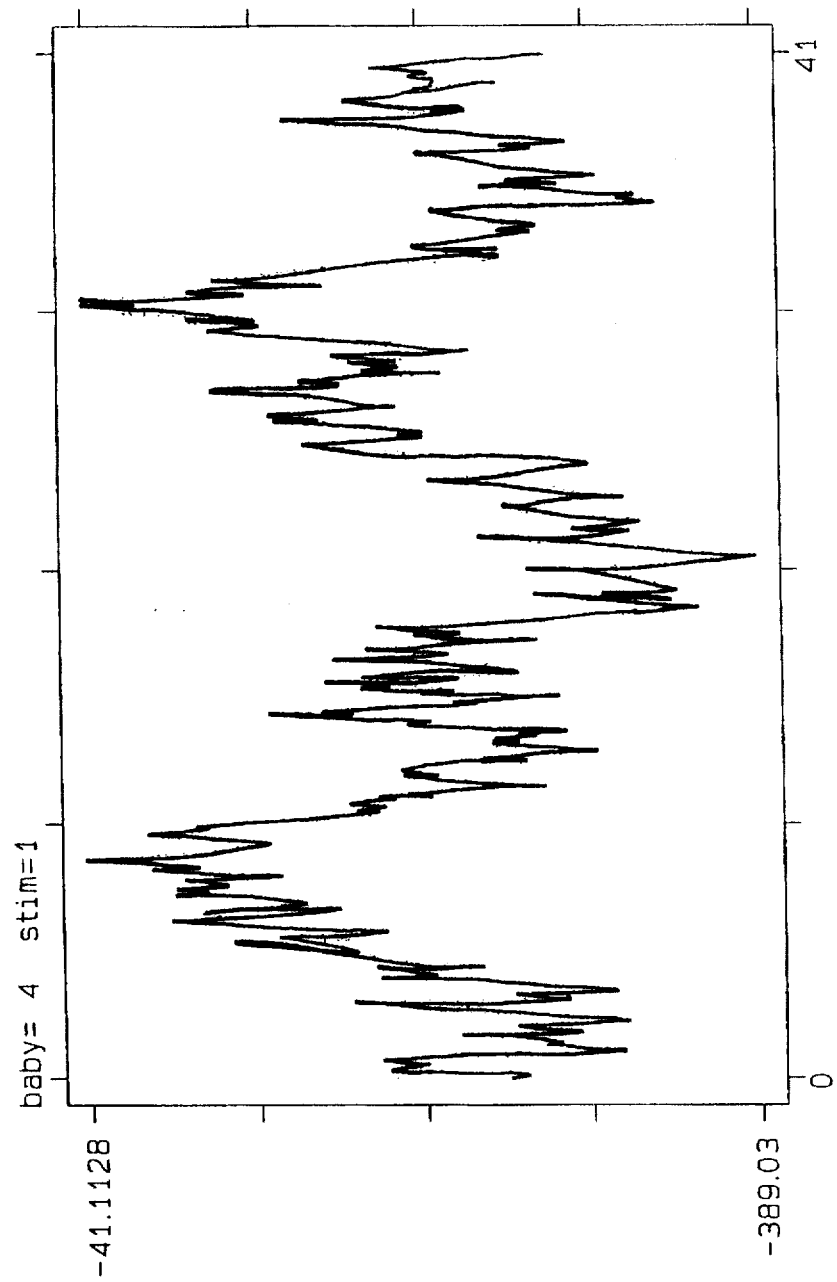

FIG. 7, which utilizes the parameters of the HEI system (2–35 msec window, weighing by 1/Var(sp)), suggests that none of the statistics perform well. Of particular concern are the false passes of which there are 4/50 for FSP. FIGS. 10a–d are plots of the average waveforms for these 4 babies (FIG. 10).

Figure 9:
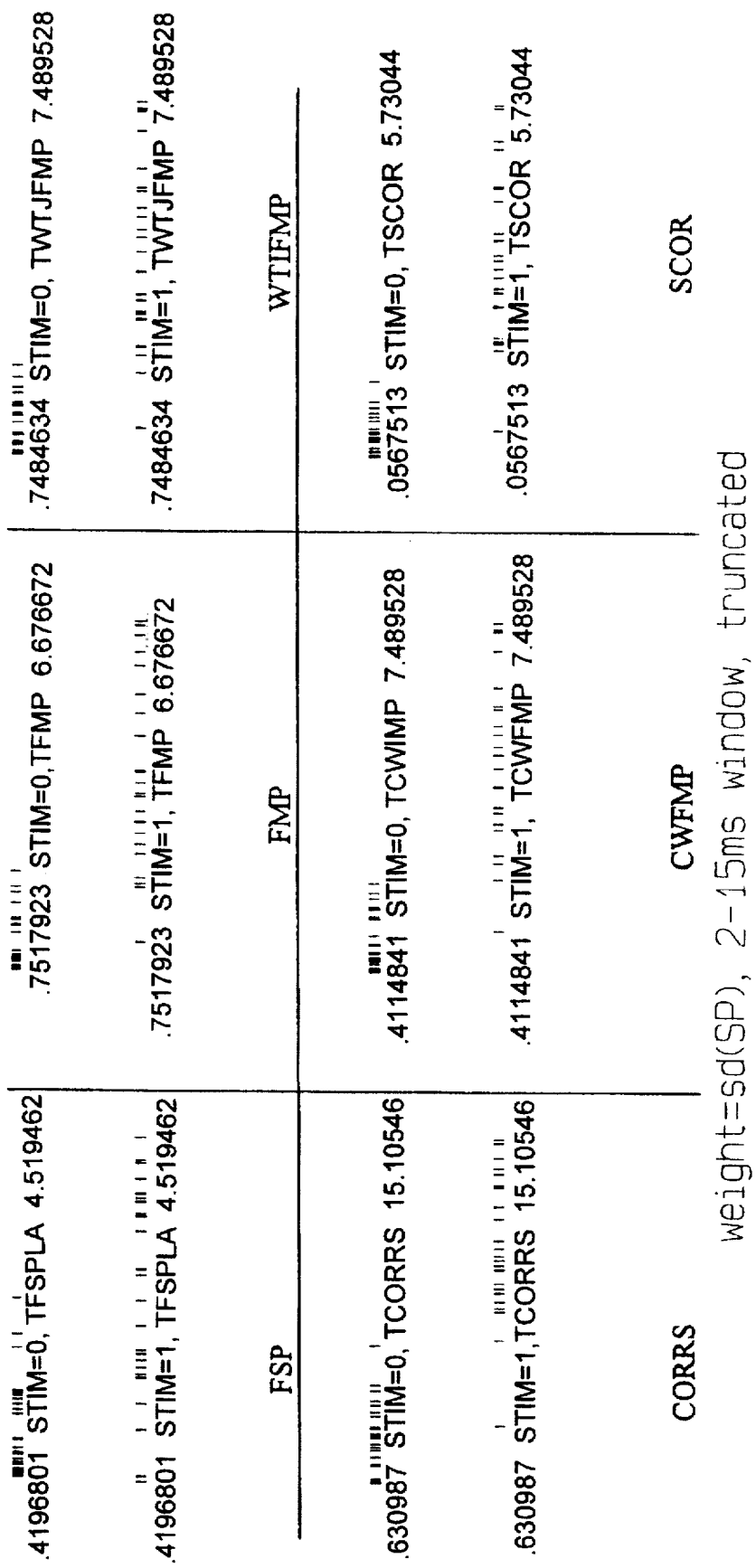

The false-pass problem is reduced considerably by using a shorter window. FIGS. 8 and 9 show plots of these statistics calculated using data from the shorter 2–15 msec window. The weighing scheme (1/Var(sp) or 1/sd(sp)) did not make much difference. FIG. 9 which uses 1/sd(sp) is preferable for theoretical reasons.

Figure 13:
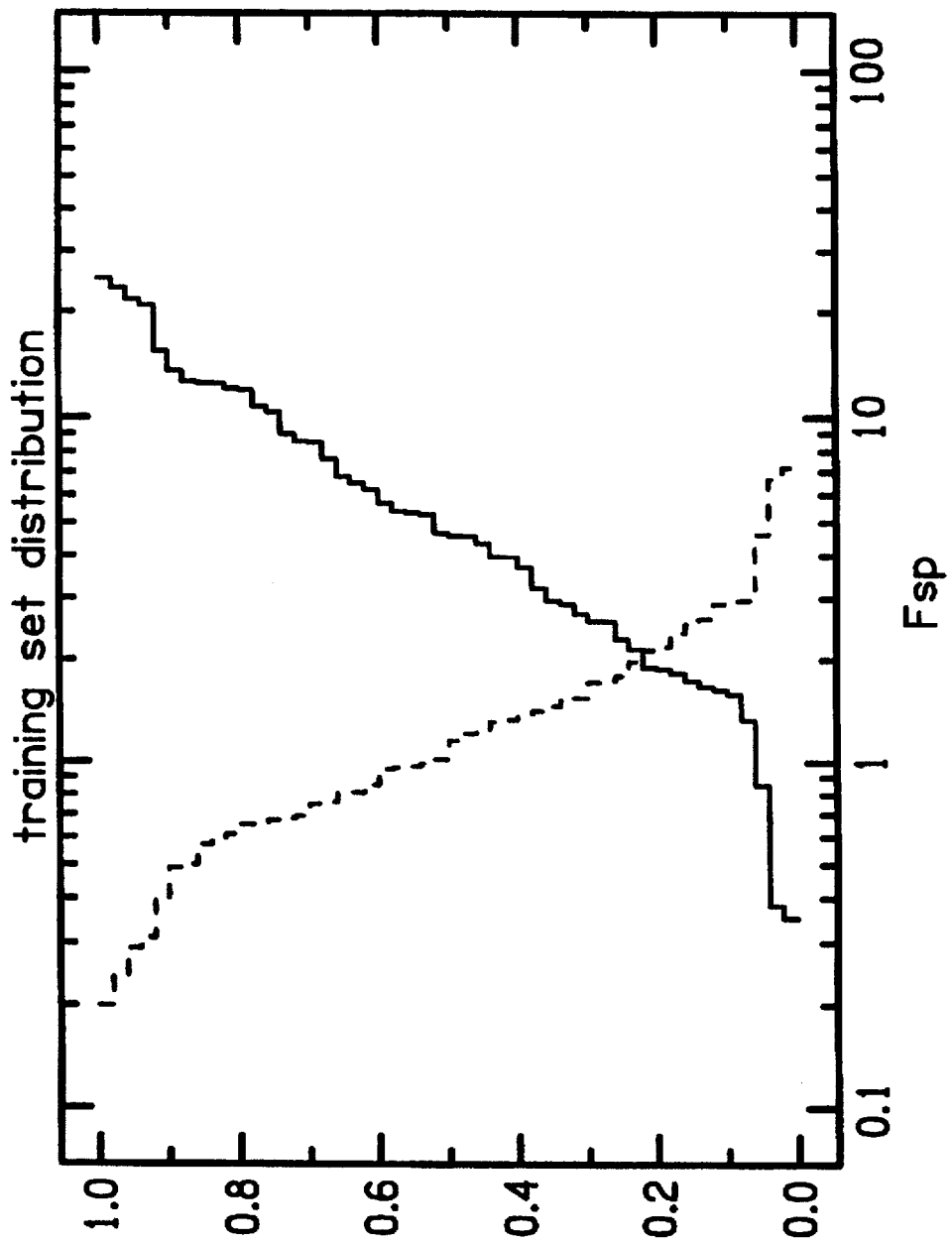

The prior art FSP statistic doesn't discriminate well between the stim and no-stim files. This data is illustrated in FIG. 13. As seen in the figure, the distributions of the statistic in the two groups overlap to a large degree. This overlap area 50 is shaded in FIG. 13. With a pass defined as exceeding the critical value of 2.4, 11(22%) of the 50 stim files failed the test. Moreover, one of the no-stim files yielded an FSP value >2.4.

FMP performed better, with 4/50 false fails, where a pass was defined as FMP>2.4. The one false pass remained (FMP=2.43). Although FMP seems to perform better, it is still not good enough.

Figure 14:
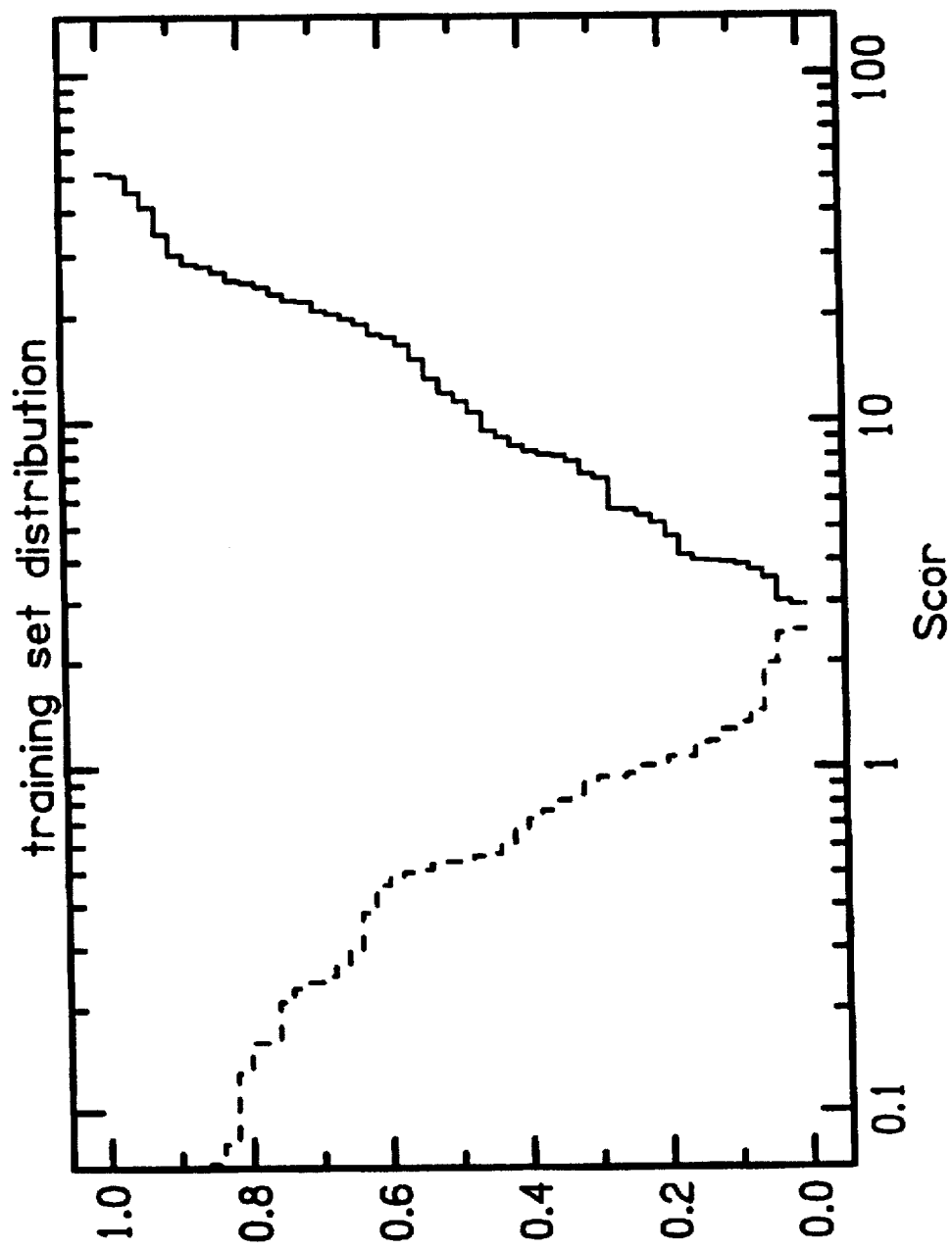

The template matching SCOR statistic of the present invention has a substantially better performance. It seems to discriminate almost perfectly between the stim and no stim files. The one false fail may have resulted from a probe slip and the unsmoothed waveform for this baby has also been plotted. If this one baby is ignored, then the maximum SCOR value at 4000 sweeps amongst the 50 no-stim files is 1.26 and the minimum amongst the stim files is 1.76. The midpoint, approximately 1.5, might be taken as the critical value for passing the test. As mentioned above, however, the selection of the SCOR threshold value representing the point at which good hearing is identified is dependent on the signal processing which is performed on the data. In other tests where additional digital filtering was accomplished to remove some higher frequency components present in the data, a threshold value of 2.7 was found to be best in discriminating between the good and bad hearing. When this filtering was applied to the test data above, the preferred threshold value was found to be 2.7. A plot of the data after application of the filtering is illustrated in FIG. 14. As seen in this figure, a value of 2.7 separates the "nonhearing" data on the left of the graph from the "hearing" data on the right. Again, the important point is not that a universally correct threshold number exists but rather that a value can be selected, based on the signal processing desired, which will separate the hearing and non-hearing groups.

Digital filtering of the recorded EP waveform was found to increase the separation of the distributions of SCOR values for the stimulated and non-stimulated conditions. Presumably, the filtering was beneficial because it effectively increased the overall signal-to-noise ratio. The digital filter was implemented in a way that did not alter the temporal location of the ABR peaks. This is important because the location of the peaks is considered clinically significant. The filter was implemented in three steps: (1) a discrete Fourier transform of the waveform was computed, (2) the frequency components were multiplied by a filter function H(f), and (3) an inverse discrete Fourier transform was computed on the result. The filter function was chosen to be real-valued function in order to avoid any phase shifts in the frequency domain that would result in temporal shifts in the waveform. The specific filter function implemented was $$H(F) = \frac{1}{1 + \left\{\frac{f_1}{f}\right\} + \left\{\frac{f}{f_2}\right\}^{16}}$$

although other similar functional forms might be equally effective. This filter function reduces both low frequencies below $f_1$ and high frequencies above $f_2$. The low frequencies are attenuated by this function at the rate of 6 dB/octave; whereas, the high frequencies are attenuated at the rate of 96 dB/octave.

SCOR was calculated on these same baby files using 1000, 2000, 3000 and 4000 sweeps. The maximum value over all four sweep #'s among the 50 no-stim files was 1.36. If the test is stopped once scor exceeds 1.5, no false passes would result. The following Table 3 illustrates the distribution of number of sweeps for the stim data sets.

TABLE 3

|  | Number of Sweeps | | | |
| --- | --- | --- | --- | --- |
|  | 1000 | 2000 | 3000 | 4000 |
| No. of babies passed | 29 | 35 | 47 | 49 |
| No. of babies not yet passed | 21 | 15 | 3 | 1 |
| Total | 50 | 50 | 50 | 50 |

The above test results clearly indicate that the SCOR ABR signal detection algorithm is extremely effective at discriminating between the hearing and nonhearing test subjects. It is also clearly evident that the SCOR detection algorithm can be used to minimize the amount of time which it takes to complete the test and arrive at a conclusion as to hearing capacity.

It is obvious that numerous other modifications and variations of the present invention are possible in view of the above teachings. For example, numerous of the hardware elements may be modified and still meet the invention's objectives. Additionally, the data may be subject to various digital filtering in an effort to remove high or low frequency noise in the system. As mentioned, this may result in the need to adjust the threshold value to accommodate shifts in the data.

Therefore it is to be understood that the above description is in no way intended to limit the scope of protection of the claims and is representative of only one of several possible embodiments of the present invention.

There has thus been shown and described an invention which accomplishes at least all of the stated objects.

We claim:

1. An improved method of gathering and analyzing auditory brainstem response (ABR) signal data generated in response to hearing stimuli to objectively determine the hearing capacity of an individual based on a correlation between the generated ABR data and a benchmark waveform, comprising:

generating a plurality of said hearing stimuli;

transmitting said plurality of stimuli to said individual;

receiving said ABR signal data from said individual in response to said plurality of stimuli, said ABR signal data defining a series of ABR waveforms, each of said waveforms being associated with a respective one of said plurality of stimuli;

forming a concurrent replication of said series of ABR waveforms by maintaining two buffers, each of said buffers comprising ABR signal data from alternating ABR waveforms; and analyzing said concurrent replications of said series of ABR waveforms to determine the hearing capacity of said individual by comparing said concurrently replicated ABR waveforms to said benchmark waveform.

2. The method of claim 1 wherein the step of analyzing said concurrently replicated waveforms includes comparing said waveforms with each other for any discrepancies therebetween.

3. The method of claim 1 wherein the step of receiving said ABR data includes the steps of:

continuously sampling said ABR signal data at a plurality of discrete time intervals between said transmission of said plurality of hearing stimuli, creating a series of sampled ABR data points associated with each of said hearing stimuli, each series of sampled data points associated with a respective one of said hearing stimuli defining an individual ABR waveform sweep;

storing said individual ABR waveform sweep of sampled ABR data points;

defining a block of data comprising a plurality of sweeps; and computing the numerical average of each of said sampled ABR data points in each of said sweeps within each of said blocks, defining an averaged block.

4. An improved method of gathering and analyzing auditory brainstem response (ABR) signal data generated in response to hearing stimuli to objectively determine the hearing capacity of an individual based on a correlation between the generated ABR data and a benchmark waveform, comprising:

generating a plurality of said hearing stimuli;

transmitting said plurality of stimuli to said individual;

receiving said ABR signal data from said individual in response to said plurality of stimuli, said ABR signal data defining a series of ABR waveforms, each of said waveforms being associated with a respective one of said plurality of stimuli;

forming a concurrent replication of said series of ABR waveforms by maintaining two buffers, each of said buffers comprising ABR signal data from alternating ABR waveforms;

analyzing said concurrent replications of said series of ABR waveforms to determine the hearing capacity of said individual by comparing said concurrently replicated ABR waveforms to said benchmark waveform;

said step of analyzing said concurrently replicated waveforms including comparing said waveforms with each other for any discrepancies therebetween; and said step of receiving said ABR data including the steps of:

continuously sampling said ABR signal data at a plurality of discrete time intervals between said transmission of said plurality of hearing stimuli, creating a series of sampled ABR data points associated with each of said hearing stimuli; each series of sampled data points associated with a respective one of said hearing stimuli defining an individual ABR waveform sweep;

storing said individual ABR waveform sweep of sampled ABR data points;

defining a block of data comprising a plurality of sweeps; and computing the numerical average of each of said sampled ABR data points in each of said sweeps within each of said blocks, defining an averaged block; and said step of analyzing said concurrently replicated ABR data waveforms including computing an ABR signal-to-noise ratio wherein a noise estimate is established as the statistical variance between said averaged blocks computed at at least one point in said sweep and further comprising the steps of reducing said concurrently replicated ABR waveforms by said noise estimate prior to analyzing said ABR waveforms.

5. The method of claim 4 wherein the step of computing said ABR signal-to-noise ratio comprises:

computing a reproduceability factor defined by the cross-correlation between each of said concurrent replications of said series of ABR waveforms;

defining a time interval window comprising a plurality of sampled ABR signal data points within a single ABR waveform;

computing a signal plus noise estimate defined as the statistical variance between said sampled ABR signal data points within said time interval window; and computing a signal for said ABR signal-to-noise ratio by multiplying said signal plus noise estimate by said reproduceability factor.

6. The method of claim 5 wherein the step of computing said signal plus noise estimate is accomplished using ABR signal data points comprising the average of said ABR signal data comprising said two concurrent replications of said series of ABR waveforms, said average of said concurrent replications of said series of ABR waveforms defining a final averaged waveform.

7. The method of claim 6 further comprising the step of digitally filtering said average of said concurrent replications of said series of ABR signal data comprising said final averaged waveform prior to computing said signal plus noise estimate.

8. The method of claim 4 further comprising the steps of defining a time interval window comprising a plurality of sampled ABR signal data point within a single ABR waveform;

computing a signal plus noise estimate defined as the statistical variance between said ABR signal data points within said time interval window;

providing a waveform template defined as an average ABR waveform from normal hearing individuals;

averaging said ABR signal data points comprising said concurrent replications of said series of ABR waveforms, defining a final averaged waveform;

computing a cross-correlation between said final average waveform and said waveform template; and computing a signal for said ABR signal-to-noise ratio by multiplying said signal plus noise estimate by said cross-correlation between said template and said final averaged waveform.

9. The method of claim 8 further comprising the step of determining a threshold value, comparing said signal thereto, the exceeding of which by said signal being indicative of normal hearing capacity.

10. The method of claim 9 wherein said threshold value is 1.5.

11. The method of claim 4 wherein the noise estimate of said signal-to-noise ratio is computed according to the formula $$RN_c(I) = RN_{max}\left\{1 + 2\sum_{i=1}^{I}\left(1-\frac{i}{N}\right)\hat{\rho}(i)\right\},$$

where:

I is the number of sweeps in the averaging function,

N is the total number of sweeps, i is the sweep index within I, $$RN_{max} \text{ is } \frac{1}{N}\left\{\sum_{K=1}^{N}\frac{(s_K-\bar{s})^2}{N}\right\},$$

$$\hat{\rho}(i) \text{ is } \frac{\sum_{k=1}^{N-i}\frac{(s_k-\bar{s})(s_{k+i}-\bar{s})}{N-i}}{\sum_{k=1}^{N}\frac{(s_k-\bar{s})^2}{N}},$$

k is the sweep index within N, $s_k$ is a data point in the $k^{th}$ sweep, and $\bar{s}$ is the average of $s_k$ over all N sweeps.

12. The method of claim 5 wherein said noise estimate of said signal-to-noise ratio is computed according to the formula:

$$RN_{BM}(B) = \frac{1}{N_B}\left\{\sum_{b=1}^{N_B}\frac{(\bar{S}_b-\bar{S})^2}{N_B}\right\}.$$

where:

B is the block size,

N is the number of sweeps, $N_B$ is N/B, $$\bar{s} \text{ is } \sum_{b=1}^{N_B}\frac{\bar{s}_b}{N_B}, \text{ and}$$

$\bar{s}$ is average waveform in block at b.

13. The method of claim 12 wherein the step of computing said signal plus noise estimate is accomplished using ABR signal data points comprising the average of said ABR signal data points comprising said two concurrent replications of said series of ABR waveforms, said average of said concurrent replications of said series of ABR waveform defining a final averaged waveform.

14. The method of claim 13 further comprising the step of digitally filtering said ABR signal data comprising said final averaged waveform prior to computing said signal plus noise estimate.

15. The method of claim 8 wherein said signal-to-noise ratio is computed according to the formula:

$$SCOR = FMP \times \Sigma(\mu_i - \bar{\mu})/\sqrt{\Sigma(\mu_i - \bar{\mu})^2(\bar{s}_i-\bar{s})^2}$$

where i indexes a point in the time window, $\mu_i$ is the template waveform at i, $\bar{\mu}$ is the template average in the window, $\bar{s}_i$ is the average waveform at i, $\bar{s}$ is the average $\bar{s}_i$ over the time window, where FMP is defined as $$FMP = \left\{\sum^{m}(\bar{S}_i-\bar{S})^2/m\right\}/Ave\{RN_{BM}(100)/NB\}$$

and $$RN_{BM}(B) = \frac{1}{N_B}\left\{\sum_{b=1}^{N_B}\frac{(\bar{S}_b-\bar{S})^2}{N_B}\right\},$$

where:

B is the block size,
N is the number of sweeps,
$N_B$ is N/B, $\bar{s}$ is $\sum_{b=1}^{N_B} \frac{\bar{s}_b}{N_B}$, and $\bar{s}$ is average waveform in block at b.

16. The method of claim 15 further comprising the step of determining a threshold value, comparing said signal-to-noise ratio thereto, the exceeding of which by said signal-to-noise ratio being indicative of normal hearing capacity.

17. The method of claim 16 wherein said threshold value is 1.5.

18. An improved apparatus for gathering and analyzing auditory brainstem response (ABR) signal data generated in response to hearing stimuli to objectively determine the hearing capacity of an individual based on a correlation between the generated ABR data and a benchmark waveform comprising:

means for generating a plurality of said hearing stimuli;
  means for transmitting said plurality of stimuli to said individual;
  means for receiving said ABR signal data from said individual in response to said plurality of stimuli, said ABR signal data defining a series of ABR waveforms, each of said waveforms being associated with a respective one of said plurality of stimuli;
  means for forming a concurrent replication of said series of ABR waveforms by maintaining two buffers, each of said buffers comprising ABR signal data from alternating ABR waveforms; and
  means for analyzing said concurrently replicated ABR waveforms to determine the hearing capacity of said individual.

19. The apparatus of claim 18 wherein said means for receiving said ABR data further comprises:

means for continuously sampling said ABR signals at a plurality of discrete time intervals between said transmission of each of said plurality of hearing stimuli, creating a series of sampled data points associated with each of said hearing stimuli, each series of data points defining an individual ABR waveform sweep;
  means for storing said sweep of sampled ABR data points;
  means for defining a block of data comprising a plurality of sweeps; and
  means for computing the numerical average of each of said sampled ABR data points in each of said sweeps within each of said blocks, defining an averaged block.

20. The apparatus of step 19 further comprising means for computing an ABR signal-to-noise ratio wherein said noise is estimated as the statisticompvariance between said averaged blocks computed at least one point in said sweep.

21. The apparatus of claim 20 wherein said means for computing said signal-to-noise ratio comprises:

means for computing a reproduceability factor defined by the cross-correlation between each of said concurrently replicated ABR waveforms;
  means for defining a time interval window comprising a plurality of sampled ABR signal data points within a single waveform;
  means for computing a signal plus noise estimate defined as the statistical variance between said ABR signal data points within said time interval window; and
  means for computing a signal for said signal-to-noise ratio by multiplying said signal plus noise estimate by said reproduceability factor.

22. The apparatus of claim 21 wherein said means for computing said signal plus noise estimate comprises means for using ABR signal data points comprising the average of said data points comprising said two concurrently replicated ABR waveforms, said average of said concurrently replicated ABR waveform defining a final averaged waveform.

23. The apparatus of claim 22 further comprising means for digitally filtering said ABR signal data comprising said final averaged waveform prior to computing said signal plus noise estimate.

24. The apparatus of claim 20 further comprising:

means for defining a time interval window comprising a plurality of sampled ABR signal data point within a single waveform;
  means for computing a signal plus noise estimate defined as the statistical variance between said ABR signal data points within said time interval window;
  means for providing a waveform template defined as an average ABR waveform from normal hearing individuals;
  means for averaging said data points comprising said concurrently replicated ABR waveforms, defining a final averaged waveform;
  means for computing a cross-correlation between said final average waveform and said waveform template; and
  means for computing a signal for said signal-to-noise ratio by multiplying said signal plus noise estimate by said cross-correlation between said template and said final averaged waveform.

25. The apparatus of claim 24 further comprising a means for determining a threshold value, comparing said signal thereto, the exceeding of which by said signal being indicative of normal hearing capacity.

26. The apparatus of claim 25 wherein said threshold value is 1.5.

27. The apparatus of claim 20 wherein said means for computing said signal-to-noise ratio comprises a means for computing said noise ratio according to the formula $$RN_c(I) = RN_{mes} \left\{ 1 + 2 \sum_{i=1}^{I} \left( 1 - \frac{i}{N} \right) \hat{\rho}(i) \right\}.$$

where:

I is the number of sweeps in the averaging function,
N is the total number of sweeps,
i is the sweep index within I, $$RN_{mes} \text{ is } \frac{1}{N} \left\{ \sum_{K=1}^{N} \frac{(s_K - \bar{s})^2}{N} \right\},$$

$$\hat{\rho}(i) \text{ is } \frac{\sum_{k=1}^{N-i} \frac{(s_k - \bar{s})(s_{k+i} - \bar{s})}{N-i}}{\sum_{k=1}^{N} \frac{(s_k - \bar{s})^2}{N}},$$

k is the sweep index within N,
$s_k$ is a data point in the $k^{th}$ sweep, and
$\bar{s}$ is the average of $s_k$ over all N sweeps.

28. The apparatus of claim 21 wherein said means for computing said signal-to-noise ratio comprises a means for computing said noise ratio according to the formula $$RN_{BM}(B) = \frac{1}{N_B} \left\{ \sum_{b=1}^{N_B} \frac{(\bar{S}_b - \bar{S})^2}{N_B} \right\}.$$

where:
B is the block size,
N is the number of sweeps,
$N_B$ is N/B, $$\bar{s} \text{ is } \sum_{b=1}^{N_B} \frac{\bar{s}_b}{N_B}, \text{ and}$$

$\bar{s}$ is average waveform in block at b.

29. The apparatus of claim 28 wherein said means for computing said signal plus noise estimate comprises means for using ABR signal data points comprising the average of said data points comprising said two concurrently replicated ABR waveforms, said average of said concurrently replicated ABR waveform defining a final averaged waveform.

30. The apparatus of claim 29 further comprising means for digitally filtering said ABR signal data comprising said final averaged waveform prior to computing said signal plus noise estimate.

31. The apparatus of claim 24 wherein said means for computing said signal-to-noise ratio comprises a means for computing said ratio according to the formula $$SCOR = FMP \times \Sigma(\mu_i - \bar{\mu}) / \sqrt{\Sigma (\mu_i - \bar{\mu})^2 (\bar{s}_i - \bar{s})^2}$$

where:
i indexes a point in the time window,
$\mu_i$ is the template waveform at i,
$\bar{\mu}$ is the template average in the window,
$\bar{s}_i$ is the average waveform at i,
$\bar{s}$ is the average $\bar{s}_i$ over the time window,
FMP is defined as $$FMP = \left\{ \sum_{i}^{m} (\bar{S}_i - \bar{S})^2 / m \right\} / Ave\{RN_{BM}(100)/NB\}$$

where:
B is the block size,
N is the number of sweeps,
$N_B$ is N/B, $$\bar{s} \text{ is } \sum_{b=1}^{N_B} \frac{\bar{s}_b}{N_B}, \text{ and}$$

$\bar{s}$ is average waveform in block at b.

32. The apparatus of claim 31 further comprising a means for determining a threshold value, comparing said signal-to-noise ratio thereto, the exceeding of which by said signal-to-noise ratio being indicative of normal hearing capacity.

33. The apparatus of claim 32 wherein said threshold value is 1.5.

34. The apparatus of claim 18 wherein said means for generating a plurality of hearing stimuli is a tone generator.

35. The apparatus of claim 18 wherein said means for transmitting said stimuli is a set of headphones.

36. The apparatus of claim 35 wherein said means for receiving and processing said ABR signal data includes a plurality of scalp electrodes secured at the mastoid and vertex regions of the head and connected to a digital signal processing board.

37. The apparatus of claim 18 wherein said computing means is an arithmetic logic unit.

38. An auditory test unit for objectively determining the hearing capacity of a test individual by using samples of the auditory brainstem response of the individual to hearing stimuli comprising:

means for generating said hearing stimuli and transmitting said stimuli to said individual;

means for receiving i samples of said auditory brainstem response signal data associated with each of said hearing stimuli wherein each of said samples is identified as $s_i$ and wherein each of said series of i samples associated with each of said stimuli comprises a waveform;

means for grouping a plurality of said waveforms into a block of waveforms;

means for grouping a plurality of said samples in each of said waveforms in a window;

means for averaging said group of samples in said window to establish an average as $\bar{s}$;

means for computing a signal estimate by summing the variance between the average signal value at point i, $s_i$, and the average signal value in said window $\bar{s}$ in the form $$\sum_{i=1}^{m} \frac{(\bar{s}_i - \bar{s})^2}{m}$$

where m is the number of windows;

means for estimating a noise component by computing the statistical variance within said block of waveforms and dividing by the number of blocks as $$Ave \left\{ \frac{RN_{BM}(100)}{NB} \right\}$$

where:
B is the block size,
N is the number of sweeps,
$N_B$ is N/B, $$\bar{s} \text{ is } \sum_{b=1}^{N_B} \frac{\bar{s}_b}{N_B}, \text{ and}$$

$\bar{s}$ is average waveform in block at b, and
B=100;

means for computing a signal-to-noise ratio by dividing said signal estimate by said noise component;

means for receiving and processing said auditory brainstem response signal data;

means for calculating an estimated residual noise present in the auditory brainstem response signal data;

means for compensating said auditory brainstem response signal data for said estimated residual noise thereby establishing a compensated auditors brainstem response;

means for computing the statistical correlation of said compensated auditory brainstem response; and means for comparing said statistical correlation to a predetermined threshold value and outputting an indication of said correlation exceeding said threshold value.

39. An improved method of gathering and analyzing auditory brainstem response (ABR) signal data to objectively determine the hearing capacity of an individual, comprising:

generating a plurality of said hearing stimuli;

transmitting said stimuli to said individual;

receiving said ABR signal data, said ABR signal data defining a series of ABR waveforms, each of said waveforms being associated with a respective one of said stimuli;

continuously sampling said ABR signal data at a plurality of discrete time intervals between said plurality of hearing stimuli, creating a series of sampled data points associated with each of said hearing stimuli, each series of sampled data points defining an individual ABR waveform sweep;

storing said ABR waveform sweep of sampled ABR data points;

defining a block of data comprising a plurality of ABR waveform sweeps; and computing the numerical average of each of said sampled data points in each of said sweeps within each of said blocks, defining an averaged block;

defining a time interval window comprising a plurality of sampled data points within a single waveform;

computing a signal plus noise estimate defined as the statistical variance between said sampled data points within said time interval window;

providing a waveform template defined as an average ABR waveform from normal hearing individuals;

averaging said data points comprising said concurrently replicated ABR waveforms, defining a final averaged waveform;

computing a cross-correlation between said final averaged waveform and said waveform template;

computing a signal for a signal-to-noise ratio by multiplying said signal plus noise estimate by said cross-correlation between said waveform template and said final averaged waveform; and analyzing said concurrently replicated ABR waveforms to determine the hearing capacity of said individual by computing a signal-to-noise ratio wherein said noise is defined as the statistical variance between said averaged blocks computed at least one point in said sweep.

* * * * *